US009987202B2

(12) United States Patent
Malle et al.

(10) Patent No.: US 9,987,202 B2
(45) **Date of Patent: *Jun. 5, 2018**

(54) ANHYDROUS SOLID COMPOSITION BASED ON PARTICLES ENCAPSULATING A BENEFICIAL AGENT

(71) Applicant: L'Oreal, Paris (FR)

(72) Inventors: Gérard Malle, Villiers S/Morin (FR); Tiina Luukas, Sevran (FR); Didier Laverre, Chevilly la Rue (FR); Isabelle Bara, La Verenne St Hilaire (FR)

(73) Assignee: L'OREAL, Paris (FR)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/324,125

(22) PCT Filed: Jul. 1, 2015

(86) PCT No.: PCT/EP2015/065010

§ 371 (c)(1),
(2) Date: Jan. 5, 2017

(87) PCT Pub. No.: WO2016/005250

PCT Pub. Date: Jan. 14, 2016

(65) Prior Publication Data

US 2017/0196781 A1 Jul. 13, 2017

(30) Foreign Application Priority Data

Jul. 9, 2014 (FR) ..................................... 14 56634

(51) Int. Cl.

| | |
|---|---|
| ***A61K 8/11*** | (2006.01) |
| ***A61K 8/92*** | (2006.01) |
| ***A61K 8/34*** | (2006.01) |
| ***A61K 8/73*** | (2006.01) |
| ***A61Q 13/00*** | (2006.01) |
| ***A61Q 15/00*** | (2006.01) |

(52) U.S. Cl.

CPC ................ *A61K 8/11* (2013.01); *A61K 8/345* (2013.01); *A61K 8/732* (2013.01); *A61K 8/738* (2013.01); *A61K 8/92* (2013.01); *A61Q 13/00* (2013.01); *A61Q 15/00* (2013.01); *A61K 2800/56* (2013.01)

(58) Field of Classification Search

None

See application file for complete search history.

(56) References Cited

U.S. PATENT DOCUMENTS

| | | | | |
|---|---|---|---|---|
| 3,971,852 | A * | 7/1976 | Brenner | A23G 3/346 264/4.6 |
| 5,506,353 | A * | 4/1996 | Subramaniam | A23L 27/70 424/49 |
| 5,508,259 | A | 4/1996 | Holzner et al. | |
| 6,200,949 | B1 | 3/2001 | Reijmer et al. | |
| 2004/0029750 | A1 | 2/2004 | Schudel et al. | |
| 2017/0189282 | A1* | 7/2017 | Malle | A61K 8/11 |
| 2017/0202755 | A1* | 7/2017 | Malle | A61K 8/11 |
| 2017/0209361 | A1* | 7/2017 | Malle | A61K 8/92 |

FOREIGN PATENT DOCUMENTS

| | | | | |
|---|---|---|---|---|
| DE | 10-2008-035013 A1 | | 1/2010 | |
| JP | 2008 156236 | * | 7/2008 | A61K 8/02 |
| JP | 2008-156236 A | | 7/2008 | |

OTHER PUBLICATIONS

Martin et al., "Encapsulation and Co-Precipitation Process with Supercritical Fluids: Application with Essential Oils", The Open Chemical Engineering Journal, 2010, 4, 31-41.

* cited by examiner

*Primary Examiner* — Aradhana Sasan
(74) *Attorney, Agent, or Firm* — Polsinelli PC

(57) ABSTRACT

Provided is a solid anhydrous composition that comprises particles comprising a core containing at least one beneficial agent and an envelope surrounding the core. The envelope comprises at least one hydrophobically modified polysaccharide and at least one water-soluble carbohydrate and/or water-soluble polyol. The particles simultaneously have a poured powder density ranging from 300.0 g/l to 600.0 g/l and an absolute density of greater than 1.0. The envelope also comprises at least one structuring agent. Also provided is a cosmetic process for caring for and/or for the hygiene of and/or for conditioning and/or for fragrancing and/or for making up keratin material. The process comprises applying to the keratin material the above composition. Also provided is a cosmetic process for treating body odor and optionally human perspiration, which comprises applying to a keratin material a composition defined above comprising at least one deodorant and/or antiperspirant in free form and/or in encapsulated form.

21 Claims, No Drawings

ANHYDROUS SOLID COMPOSITION BASED ON PARTICLES ENCAPSULATING A BENEFICIAL AGENT

CROSS REFERENCE TO RELATED APPLICATIONS

This application is a National Phase filing under 35 U.S.C. § 371 of PCT/EP2015/065010 filed on Jul. 1, 2015; and this application claims priority to Application No. 1456634 filed in France on Jul. 9, 2014 under 35 U.S.C. § 119. The entire contents of each application are hereby incorporated by reference.

The present invention relates to a solid anhydrous composition comprising:

1) at least particles comprising a core containing at least one beneficial agent and an envelope surrounding the core; said envelope comprising at least one hydrophobic-modified polysaccharide and at least one water-soluble carbohydrate and/or water-soluble polyol;

said particles simultaneously having a poured powder density ranging from 300.0 g/l to 600.0 g/l and an absolute density of greater than 1.0; and 2) at least one structuring agent.

The invention also relates to a cosmetic process for caring for and/or for the hygiene of and/or for conditioning and/or for fragrancing and/or for making up a keratin material, which consists in applying to said keratin material a composition as defined previously.

The present invention also relates to a cosmetic process for treating body odor and optionally human perspiration, which consists in applying to a keratin material a composition as defined previously comprising at least one deodorant active agent and/or antiperspirant active agent in free form and/or in encapsulated form.

Many cosmetic presentation forms can deliver beneficial agents, especially in cosmetic products equally including formulations for caring for and/or for the hygiene of and/or for making up the skin, the nails, the eyelashes, the eyebrows or the hair; fragrancing products; oral hygiene products such as mouth care products, deodorizers such as chewing gums, candy and pastilles for the breath; pharmaceutical products; products for veterinary use such as animal litters; animal hygiene and/or care products; household maintenance products such as laundry care and/or cleansing products (washing products, fabric softeners), washing-up products, products for cleaning and/or maintaining household electrical appliances, products for cleaning and/or maintaining floors, tiles, wood, etc.; sanitary products such as deodorizers, descaling products, pipework unblocking products; textile maintenance products; maintenance products for leather goods such as shoes and soles; products derived from the food industry; products derived from agriculture; plant protection products; products derived from the wood and paper industry.

Among these, solid compositions constitute a category of products that are appreciated by consumers for their ease of use, storage and conservation. They are widely used in the food industry (confectionery or biscuit manufacture), in textile maintenance products (waxing products or waterproofing products) and/or also in maintenance and sanitary products (soaps, deodorizing blocks or descaling blocks).

In cosmetics, they are used in particular in the field of deodorants and antiperspirants in the form of wands or sticks, but may also be profitably exploited in products for making up or caring for human keratin materials such as the skin or the lips, such as lipsticks, foundations cast in stick or dish form, face powders or eyeshadows, concealer sticks, lip glosses, eyeliners, mascaras, lipcare balms or bases, body ointments, daily care balms or bases, or alternatively antisun or self-tanning sticks.

The aim of the present invention is to propose novel compositions of anhydrous solid type comprising at least one beneficial agent encapsulated in particles that are leaktight in the absence of moisture, i.e. odorless if the active agent is a perfume said particles having a low poured powder density to facilitate their formulation and to conserve a soft, light texture said particles also needing to be compatible with the usual ingredients for these formulations and strong enough to be able to be formulated in solid form without being damaged said beneficial agent contained in the particles being able to be released virtually immediately, gradually and repeatably on the skin, the hair and the integuments on contact with water.

It is known that there is a need in many industrial fields to protect a certain number of fragile or volatile molecules and to control their release into an external medium.

One of the means for achieving such an aim is to encapsulate them. The object of this encapsulation is to reduce the evaporation and the transfer of the active material toward the environment, either during storage or during the production of the products, or alternatively during their use. Said encapsulation may also make the material easier to use by diluting it and by promoting its uniform distribution in the support.

Microencapsulation includes all the technologies for coating or trapping active principles in solid, liquid or gaseous form inside individualized particles whose size ranges between a few microns and a few millimeters. If these microparticles are hollow (vesicular), they are referred to as microcapsules, and if they are filled (matrix-based), they are referred to as microspheres. Their size ranges from 1 μm to more than 1000 μm. These microparticles may or may not be biodegradable and may contain between 5% and 90% (by mass) of active substance.

The encapsulated active substances are of very varied origin: pharmaceutical or cosmetic active principles, food additives, plant protection products, fragranced essences, microorganisms, cells, or alternatively chemical reaction catalysts, etc.

The advantage of encapsulation microparticles lies above all in the presence of a polymer membrane, which isolates and protects the contents from the external medium. Depending on the case, the membrane will be destroyed during use to release its contents (for example: "scratch and sniff" advertising inserts which release perfume when the microcapsules are crushed), or alternatively the membrane will remain throughout the release of the contents, the rate of diffusion of which it will control (for example: encapsulation of medicaments for sustained release).

The coating materials are generally hydrophobic or hydrophilic polymers of natural or synthetic origin, or alternatively lipids.

The main processes for performing the encapsulation of substances in microparticles are interfacial polymerization, interfacial crosslinking, emulsification followed by evaporation or extraction of the solvents, double emulsification evaporation/extraction of solvent, spray-drying, prilling and coacervation.

U.S. Pat. No. 5,508,259 proposes nonaqueous fragrancing compositions, comprising perfumes encapsulated in water-soluble spherical particles (capsules). Said particles are obtained via conventional encapsulation techniques and in particular the spray-drying of an emulsion formed from a film-forming solid substrate in combination with an emulsifying agent and a mixture of fragrancing ingredients. The film-forming solid substrate is especially chosen from polyvinyl acetate, polyvinyl alcohol, dextrins, natural or modified starch, plant gums, pectins, xanthans, alginates, carrageenans or alternatively cellulose derivatives, for instance carboxymethylcellulose, methylcellulose or hydroxyethylcellulose. The emulsion is then dehydrated via a standard atomization (spray-drying) process, which consists, as described in Example 1, in spraying it as fine droplets in an atomizer at a flow rate of 50 kg/h and a pressure of 0.45 bar, in contact with an air stream at 320 $m^3$/h heated to 350° C. so as to evaporate the water, which makes it possible to obtain a fine powder with a particle diameter of between 20 and 80 microns and containing 20% by weight of perfume.

However, it was noted that the particles obtained via this process were highly odorous in dry form on account of the presence of free (non-encapsulated) perfume, that they were formed mainly from agglomerates that were liable to harm the homogeneity of the product and prevent correct application of the product, and they did not have the density characteristics suitable for the objective of the invention.

U.S. Pat. No. 6,200,949 also describes a process for forming a particulate material containing a hydrophilic perfume, comprising the successive steps consisting in forming an aqueous emulsion of perfume containing 40% to 60% by weight of water, 3% to 30% by weight of maltodextrin and 10% to 40% by weight of hydrophobically modified starch, and then drying it by spraying in an atomizer (air stream at 420 $m^3$/h heated to 204° C.) so that the particles are formed with a mean size from about 3 to about 10 microns and a perfume content of from 15% to 50% by weight. However, the particles obtained via this process are highly odorous in dry form on account of the presence of free (non-encapsulated) perfume, that they are formed mainly from agglomerates, are liable to harm the homogeneity of the product and do not have the density characteristics suitable for the objective of the invention.

It is thus very important to be able to provide leaktight particles which release their contents only on demand (in response to the ambient moisture, especially in humid climatic zones, in response to body perspiration, shampooing or showering, etc.), firstly to ensure protection over time of the encapsulated active agent, above all if it is fragile and/or volatile, and secondly to avoid interactions with the other ingredients of the formulation. When the encapsulated beneficial agent is a fragrancing ingredient and/or a whole perfume, it is all the more important for the encapsulation to be total, which leads to odorless particles in anhydrous formulations allowing the formulator to combine them, if desired, with any free perfume of his choice (identical or different) without any risk of interactions or of disruption of the chosen fragrance note.

Patent EP 1 917 098 B1 proposes a process for preparing encapsulation products by precipitation, said process using:

a pumpable emulsion comprising (i) a continuous phase containing a solvent and a solute forming a matrix dissolved in said solvent and (ii) a dispersed phase;

an extractor comprising a supercritical, subcritical or liquefied gas;

said solvent being substantially more soluble in the extractor than said solute forming a matrix, and said process comprising the successive steps consisting in:

a. combining the pumpable emulsion with the extractor under mixing conditions;

b. allowing the formation of particulate encapsulation products in which the dispersed phase is embedded in a solid matrix of the solute forming a matrix;

c. collecting the encapsulation products and separating them from the extractor.

It is indicated that this process may be used in the pharmaceutical and agrifood industries and also in the fields of agriculture, coating, adhesives and catalysts. It may be used in particular for encapsulating pharmaceutical active agents, flavorings, enzymes, dyes, pesticides and herbicides.

After extensive research, the Applicant has discovered, surprisingly and unexpectedly, that it is possible to achieve the objectives as stated previously by using, in a solid anhydrous composition comprising at least one structuring agent and particles comprising a core containing at least one beneficial agent and an envelope surrounding the core; said envelope comprising at least one hydrophobic-modified polysaccharide and at least one water-soluble carbohydrate and/or water-soluble polyol; said particles simultaneously having a poured powder density ranging from 300.0 g/l to 600.0 g/l and an absolute density of greater than 1.0. These particles may be obtained in particular via the process as described in patent EP 1 917 098 B1 as commented previously.

The particles in accordance with the present invention make it possible to encapsulate beneficial ingredients, which are in particular fragile, completely (total encapsulation), without degradation, in capsules that are strong enough and leaktight enough to be able to be stored without impairment in the absence of moisture, and which can be readily formulated and remain stable in solid anhydrous compositions. These same particles of this type of composition preferably have spherical morphology and a very low poured powder density to conserve the light and soft texture; they also have the capacity of opening in the presence of water to be able to release their beneficial agent virtually immediately, gradually and repeatably on the skin, the hair and the integuments on contact with water.

This discovery forms the basis of the present invention.

The present invention relates to a solid anhydrous composition comprising:

1) at least particles comprising a core containing at least one beneficial agent and an envelope surrounding the core; said envelope comprising at least one hydrophobic-modified polysaccharide and at least one water-soluble carbohydrate and/or water-soluble polyol;

said particles simultaneously having a poured powder density ranging from 300.0 g/l to 600.0 g/l and an absolute density of greater than 1.0; and 2) at least one structuring agent.

Preferably, the composition comprises a physiologically acceptable medium.

According to a particular form of the invention, the compositions are cosmetic or dermatological.

According to a particular form of the invention, the compositions according to the invention may be used in other industrial applications and may especially be consumer products chosen from oral hygiene products such as mouth care products, deodorizers such as chewing gums, candy and pastilles for the breath; products; products for veterinary use such as animal litters; animal hygiene and/or care products; household maintenance products such as laundry care and/or cleansing products (washing products, fabric softeners), washing-up products, products for cleaning and/or maintaining household electrical appliances, products for cleaning and/or maintaining floors, tiles, wood, etc.; sanitary products such as deodorizers, descaling products, pipework unblocking products; textile maintenance products; maintenance products for leather goods such as shoes and soles; products derived from the agrifood industry; products derived from agriculture; plant protection products; products derived from the wood and paper industry.

The invention also relates to a cosmetic process for caring for and/or for the hygiene of and/or for conditioning and/or for fragrancing and/or for making up a keratin material, which consists in applying to said keratin material a composition as defined previously.

The invention also relates to a cosmetic process for treating body odor and optionally human perspiration, which consists in applying to a keratin material a composition as defined previously comprising at least one deodorant active agent and/or antiperspirant active agent in free form and/or in encapsulated form.

The invention also relates to a consumer product, characterized in that it is formed from a composition as defined previously.

Definitions

For the purposes of the present invention, the term "anhydrous" refers to a liquid phase with a water content of less than 5% by weight, preferably less than 2% by weight and even more preferably less than 1% by weight relative to the weight of said composition, or alternatively even less than 0.5% and especially free of water, the water not being added during the preparation of the composition, but corresponding to the residual water supplied by the mixed ingredients.

For the purposes of the present invention, the term "physiologically acceptable medium" is intended to denote a medium that is suitable for the topical administration of a composition. A physiologically acceptable medium has no unpleasant odor and/or appearance, and is perfectly compatible with topical administration.

The term "keratin material" means the skin, leathers, the scalp, the lips and/or integuments such as the nails and keratin fibers, for instance bodily hair, the eyelashes, the eyebrows and head hair.

For the purposes of the invention, the term "cosmetic composition" means any composition applied to a keratin material to produce a non-therapeutic hygiene, care, conditioning or makeup effect contributing toward improving the well-being and/or enhancing the beauty and/or modifying the appearance of the keratin material onto which said composition is applied.

For the purposes of the invention, the term "dermatological composition" means any composition applied to a keratin material to prevent and/or treat a disorder or dysfunction of said keratin material.

For the purposes of the invention, the term "cosmetic care and treatment" means any non-therapeutic hygiene, care, conditioning or makeup effect contributing toward improving the well-being and/or enhancing the beauty and/or modifying the appearance of the keratin material onto which said composition is applied.

The term "consumer product" means any manufactured product intended to be used or consumed in the form in which it is sold and which is not intended for a subsequent manufacture or modification. Without the examples being limiting, the consumer products according to the invention may be formulations for caring for and/or for the hygiene of and/or for making up the skin, the nails, the eyelashes, the eyebrows, the hair or the scalp; fragrancing products; oral hygiene products such as mouth care products, deodorizers such as chewing gums, candy and pastilles for the breath; pharmaceutical products; products for veterinary use such as animal litters; animal hygiene and/or care products; household maintenance products such as laundry care and/or cleansing products (washing products, fabric softeners), washing-up products, products for cleaning and/or maintaining household electrical appliances, products for cleaning and/or maintaining floors, tiles, wood, etc.; sanitary products such as deodorizers, descaling products, pipework unblocking products; textile maintenance products; maintenance products for leather goods such as shoes and soles; products derived from the agrifood industry such as confectionery products (candy or chewing gums) or from biscuit manufacture; products derived from agriculture; plant protection products; products derived from the wood and paper industry.

For the purposes of the invention, the term "beneficial agent" means any chemical compound present in a consumer product which produces a beneficial effect perceived by the consumer during its use and/or obtained on the consumer product itself, said beneficial effect possibly being a sensory improvement or a modification, especially visual and/or olfactory and/or gustatory and/or tactile, an improvement in the comfort and/or ease of application, an esthetic effect, a hygiene effect, a sensation of cleanliness, or a curative and/or prophylactic effect.

The term "particles comprising a core containing at least one beneficial agent" means a particle comprising at least one beneficial agent which is immobilized, captured and/or encapsulated in the matrix of an encapsulation or trapping system; said beneficial agent being released to the exterior gradually as the encapsulation or trapping system deteriorates when its degradation takes place on contact with a medium with which it reacts or under the effect of a stimulus such as a supply of water.

The term "solid composition" means that the measurement of the maximum force measured by texturometry during the penetration of a probe into the sample of formulation must be at least equal to 0.25 newton, in particular at least equal to 0.30 newton and especially at least equal to 0.35 newton, assessed under precise measurement conditions as follows.

The formulations are poured hot into jars 4 cm in diameter and 3 cm deep. Cooling is performed at room temperature. The hardness of the formulations produced is measured after an interval of 24 hours. The jars containing the samples are characterized in texturometry using a texturometer such as the machine sold by the company Rheo TA-XT2, according to the following protocol: a stainless-steel ball probe 5 mm in diameter is brought into contact with the sample at a speed of 1 mm/s. The measurement system detects the interface with the sample, with a detection threshold equal to 0.005 newton. The probe penetrates 0.3 mm into the sample, at a speed of 0.1 mm/s. The measuring machine records the change in force measured in compression over time, during the penetration phase. The hardness of the sample corresponds to the average of the maximum force values detected during penetration, over at least three measurements.

The term "structuring agent" means any mineral or organic compound, in the form of a simple molecule or a polymer, which is capable of stiffening the composition to the point of producing a composition that is solid according to the definition given previously.

Poured Powder Density (or Loose Bulk Density)

The determination is performed at room temperature (20-25° C.) and under normal atmospheric conditions (1 atmosphere) using a 100 ml measuring cylinder. The measuring cylinder is weighed empty and then filled with a volume of 100 ml of poured powder, without tapping. The difference in mass between the empty measuring cylinder and cylinder filled with 100 ml of powder gives the poured powder density.

Absolute Density

Measurement Principle

The measurement consists in determining the weight of a sample of a solid powder by simple weighing, followed by measuring the volume occupied by the powder particles by measuring the volume of liquid displaced by the powder sample by immersion in this liquid. The liquid chosen must be sparingly volatile and must not be a solvent for the powder. Cyclohexane is generally chosen. The measurements are performed at least twice.

Materials:

A 10 or 25 ml graduated flask and a precision balance.

$m_1$ is the weight of the empty flask.

$m_2$ is the weight of the flask filled with water up to the graduation mark.

$m_3$ is the weight of the flask filled with cyclohexane up to the graduation mark.

$m_4$ is the weight of the flask filled to about one third of its volume with the powder to be analyzed.

The flask is filled to about one third of its volume with the powder to be analyzed.

Method

The flask is filled to slightly below the graduation mark with cyclohexane. In order to completely remove the air trapped in the powder, the following is performed:

1) the flask is treated in an ultrasonic bath for 5 minutes
2) the level of cyclohexane is adjusted to the graduation mark
3) the flask is treated in an ultrasonic bath for 2 minutes
4) steps 2 and 3 are repeated if necessary, until the level of the cyclohexane no longer changes.

$m_5$ is the weight of the flask thus filled.

The weight of powder analyzed is equal to $m_4-m_1$ (for good accuracy, this weight must be greater than 2 g). Since the density of air is very low relative to that of the solid, it is taken that $m_4-m_1$ is equal The weight of cyclohexane corresponding to the volume occupied by the solid (Vs) is equal to:

$$m_6=(m_3-m_1)-(m_5-m_4)=\rho_{cyclo}\cdot Vs$$

where $\rho_{cyclo}$ is the density of cyclohexane at the temperature of the laboratory.

The absolute density of the constituent solid of the powder is equal to $\rho_{cyclos}=(m_4-m_1)/Vs=\rho_{cyclo}(m_4-m_1)/m_6$.

If the density of cyclohexane at the temperature of the laboratory is unknown, it is determined as follows relative to that of water:

If Vf is the graduated volume of the flask and $\rho_{water}$ is the density of water at the temperature of the laboratory, then:

$$\rho_{cyclo}=(m_3-m_1)/Vf \text{ and } \rho_{water}=(m_2-m_1)/Vf$$

$$\text{i.e. } \rho_{cyclo}=\rho_{water}(m_2-m_1)/(m_3-m_1)$$

The absolute density of the constituent solid of the powder is equal to:

$$\rho_s=[\rho_{water}(m_4-m_1)(m_2-m_1)]/[m_6(m_3-m_1)].$$

Encapsulation Particles

The particles in accordance with the invention comprise a core containing at least one beneficial agent and an envelope surrounding the core; said envelope comprising at least one hydrophobic-modified polysaccharide and at least one water-soluble carbohydrate and/or water-soluble polyol; said particles simultaneously having a poured powder density ranging from 300.0 g/l to 600.0 g/l and an absolute density of greater than 1.0.

The term "spherical" means that the particle has a sphericity index, i.e. the ratio between its largest diameter and its smallest diameter, is less than 1.2. In this case, such particles are generally referred to as "capsules".

The term "mean size" of the particles means the parameters D[4,3] and D[2,3] measured via the dry route by laser scattering using a Microtrac S3500 particle size analyzer, the results being expressed in the form of the volume and number particle size distributions giving access to the mean diameter.

The spherical particles in accordance with the present invention thus have a number-mean diameter ranging from 1 to 30 μm, preferably ranging from 2 to 15 μm and even better still from 5 to 10 μm and a volume-mean diameter ranging from 5 to 150 μm, preferably ranging from 10 to 100 μm and even better still from 20 to 80 μm.

The particles according to the invention containing the beneficial agent preferably represent from 0.1% to 60% by weight, preferably from 0.3% to 40% by weight and better still from 0.5% to 20% by weight relative to the total weight of the composition.

Hydrophobically Modified Polysaccharide

The term "hydrophobically modified polysaccharide" means any chemically or enzymatically modified polysaccharide comprising at least one hydrophobic functional group.

Polysaccharides are carbohydrate macromolecules formed by the linking of a large number of hydrophilic elementary sugars (saccharides) bonded together via O-oside bonds.

The hydrophobic functional groups of the present invention are hydrocarbon-based groups (formed essentially from carbon and hydrogen atoms) comprising at least 4 carbon atoms, preferably at least 6 and better still at least 8 carbon atoms, such as alkyl, alkenyl, aryl (i.e. phenyl) or aralkyl (i.e. benzyl) groups. The maximum number of carbon atoms in the hydrocarbon-based group is preferably 24, more preferentially 20 and even more preferentially 18. The hydrophobic hydrocarbon-based groups may be unsubstituted, for example formed from a simple long alkyl chain, or may be substituted with unreactive groups, for instance aromatic groups such as aryl (i.e. phenyl) or aralkyl (i.e. benzyl) groups or alternatively polar groups, for instance carboxyls or hydroxyls.

To graft the hydrophobic functional group(s) onto the polysaccharides, use is generally made of halogenated derivatives, epoxides, isocyanates, or carboxylic acids or derivatives thereof (esters, acid halides or anhydrides).

Among the hydrophobically modified polysaccharides according to the invention, preference is given to hydrophobically modified neutral polysaccharides such as:

- celluloses and derivatives thereof, in particular hydrophobically modified methyl-, hydroxyethyl-, ethylhydroxyethyl-, hydroxypropyl-, hydroxypropylmethyl- and carboxymethyl-celluloses. The preferred hydrophobic groups are chosen from $C_8$-$C_{18}$ alkyl radicals and more particularly $C_{12}$-$C_{18}$ alkyl radicals. In particular, the hydrophobically modified neutral polysaccharides denote hydrophobically modified ethylhydroxyethylcellulose or hydroxyethylcellulose and especially those sold by Ashland under the trade name Natrosol Plus and those sold by AkzoNobel under the name Bermocoll EHM200;

hydrophobically modified starches and derivatives thereof (in particular: hydroxyethyl-, hydroxypropyl- and carboxymethyl-starch) and also hydrophobically modified degraded and/or esterified starches, hydrophobically modified dextrans especially such as the phenoxy-dextrans obtained by reaction between 1,2-epoxy-3-phenoxypropane and a dextran; ($C_6$-$C_{12}$) alkyl-dextrans obtained by reaction between 1,2-epoxy-($C_6$-$C_{12}$)alkanes such as 1,2-epoxyoctane or 1,2-epoxydodecane and a dextran;

hydrophobically modified guars and hydroxyethyl-, carboxymethyl- and hydroxypropyl-guar derivatives;

hydrophobically modified *pullulans* such as cholesteryl-pullulans;

inulins hydrophobically modified via alkyl ether, ester and carbamate functions, in particular carbamates bearing $C_4$-$C_{18}$ alkyl chains and more particularly those sold under the name Inutech® SP1.

The hydrophobically modified polysaccharide preferably represents from 20% to 90% by weight, especially from 30% to 80% by weight, better still from 40% to 70% by weight and even better still from 40% to 60% by weight relative to the total weight of the envelope of the particle.

According to a particularly preferred form of the invention, hydrophobically modified starches will be chosen among the hydrophobically modified polysaccharides.

The botanical origin of the starch molecules may be cereals or tubers. Thus, the starches are chosen, for example, from corn starch, rice starch, cassava starch, tapioca starch, barley starch, potato starch, wheat starch, sorghum starch and pea starch.

The term "hydrophobically modified starch" means any chemically or enzymatically modified starch comprising at least one hydrophobic functional group.

The hydrophobically modified starches in accordance with the invention are preferably chosen from C10-C18 hydroxyethyl starch esters and starch $C_5$-$C_{20}$-alkyl or $C_5$-$C_{20}$ alkenyl succinates, more particularly $C_5$-$C_{20}$-alkenyl succinates and even better still sodium starch octenyl succinate (E1450-CAS 66829-29-6/52906-93-1/70714-61-3), in particular the product sold by National Starch under the name Capsul®.

Mention may also be made of the commercial references Capsul TA®, N-LOK®, N-LOK 1930®, HI-CAP 100®, Purity Gum 1773® and Purity Gum 2000 ® from National Starch, Cleargum CO® from the company Roquette and Emcap®, Emtex® and Delitex the company Cargill.

Water-Soluble Carbohydrate or Polyol

The term "water-soluble carbohydrate" or "water-soluble polyol" refers to a carbohydrate or a polyol which, when introduced into water without pH modification at 25° C., at a mass concentration equal to 3%, makes it possible to obtain a macroscopically homogeneous and transparent solution, i.e. a solution with a minimum light transmittance value, at a wavelength equal to 500 nm, through a sample 1 cm thick, of at least 80% and preferably of at least 90%.

The term "carbohydrates" (also known as saccharides) means all simple sugars or doses and combinations thereof or osides.

Carbohydrates usually comprise:

(1) monosaccharides or oses which are of two types: aldoses comprising an aldehyde function on the first carbon and ketoses comprising a ketone function on the second carbon. They are also distinguished according to the number of carbon atoms they contain.

(2) oligosaccharides (or oligosides), which are saccharide oligomers bearing a sequence of 2 to 10 monosaccharide units linked via glycoside bonds.

(3) polyholosides (or polysaccharides or polyosides), which are saccharide polymers bearing a sequence of more than 10 monosaccharides.

Water-Soluble Carbohydrates (1) Saccharides or Monosaccharides

Among the saccharides or monosaccharides that may be used according to the invention, mention may be made, alone or as mixtures, of:

tetroses containing four carbons: erythrose, threose, erythrulose;

pentoses containing five carbons: ribose, arabinose, xylose, deoxyribose;

hexoses containing six carbons: glucose, mannose, fucose, gulose, idose, galactose, talose, fuculose, fructose, sorbose, rhamnose;

heptoses containing seven carbons: sedoheptulose in their D and/or L form.

Among the monosaccharides, use will be made more preferentially of arabinose, xylose, fructose, glucose, mannose, rhamnose or threose and even more preferentially glucose or threose.

(2) Oligosaccharides

Among the oligosaccharides that may be used according to the invention, mention may be made of:

(i) disaccharides or diholosides or diosides composed of two saccharide molecules.

Among the disaccharides, mention may be made of: cellobiose, isomaltose, isomaltulose, lactose, lactulose, maltose, sucrose, trehalose or melibiose.

(ii) triholosides composed of three saccharide molecules, for instance: raffinose or maltotriose.

(iii) dextrins, which are mixtures of linear gluco-oligosides (glucose oligosides) in which the glucose units are linked via oside bonds of the α-(1,4) or α-(1,6) type.

(iv) glucose syrups obtained by acidic or enzymatic hydrolysis of starch, the D.E. of which is between 20 and 100.

D.E. or "dextrose equivalent" is the indicator of the degree of total hydrolysis of starch. The higher the D.E., the more extensive the hydrolysis, and thus the higher the proportion of simple (short-chain) sugars.

(v) glucose-fructose syrups especially with a high content of fructose (HFCS: high-fructose corn syrup), which denote a series of corn syrups that have been subjected to enzymatic processes in order to increase their fructose content before being mixed with glucose syrup to obtain their final composition.

Among the glucose-fructose syrups, also known as isoglucose syrups, which may be used according to the invention, mention may be made of:

HFCS 90, which contains 90% fructose and 10% glucose syrup;

HFCS 55, which contains 55% fructose and 45% glucose syrup;

HFCS 42, which contains 42% fructose and 58% glucose syrup.

Among the oligosaccharides, use will be made more preferentially of cellobiose, maltose, isomaltose, raffinose and glucose syrups, more particularly glucose syrups.

Use will be made preferentially of a glucose syrup with a D.E. ranging from 21 to 60 and even more preferentially a glucose syrup with a D.E. of from 21 to 38, for instance the dehydrated glucose syrups sold by Tereos under the names G210, G290 and G380.

(3) Polysaccharides or Polyholosides

Mention may be made, for example, of:

- dextrans, which are composed of D-glucose units linked via an $\alpha(1\rightarrow6)$ oside bond and bearing branches formed from alpha 1-2 or 1-3 or 1-4 bonds. They are prepared by fermentation of beet sugar solely containing hydroxyl groups. It is possible to obtain dextran fractions of different molecular weights from native dextran by hydrolysis and purification. Dextran may in particular be in the form of dextran sulfate.
- *pullulans*, which are formed from maltotriose units, known under the name $\alpha(1,4)$-$\alpha(1,6)$-glucan. Three glucose units in maltotriose are connected via an $\alpha(1,4)$ glycoside bond, whereas the consecutive maltotriose units are connected to each other via an $\alpha(1,6)$ glycoside bond. It is produced, for example, from starch by the fungus *Aureobasidium pullulans*. Pullulan is produced, for example, under the reference Pullulan PF 20® by the company Hyashibara in Japan.
- maltodextrins, which are the result of hydrolysis of a cereal (wheat or corn) starch or of a tuber (potato) starch. They are formed from various sugars (glucose, maltose, maltotriose, oligosides and polyosides) derived directly from this reaction, in proportions which depend on the degree of hydrolysis.

This degree is measured by the "dextrose equivalent", or D.E., dextrose or D-glucose being the result of a total hydrolysis of starch. The higher the D.E., the more extensive the hydrolysis, and thus the higher the proportion of simple (short-chain) sugars of which maltodextrin is composed.

The maltodextrins used in accordance with the invention preferentially have a D.E. ranging from 4 to 20 and better still maltodextrins with a D.E. ranging from 12 to 20.

Use will preferably be made of potato or corn maltodextrins such as those sold under the trade names MD 20P® from Avebe and Maldex 120®, Maldex 170® and Maldex 190® from Tereos.

Polyols

For the purposes of the invention, polyols are linear, branched and/or cyclic, non-glycoside, saturated or unsaturated carbon-based and especially hydrocarbon-based compounds, comprising 4 to 18 carbon atoms, especially 4 to 16, or even 4 to 12 carbon atoms, and 3 to 9 hydroxyl (OH) groups, and also possibly comprising one or more oxygen atoms intercalated in the chain (ether function).

The polyols in accordance with the invention are preferably linear or branched saturated hydrocarbon-based compounds, comprising 4 to 18 carbon atoms, especially 4 to 16 or even 4 to 12 carbon atoms, and 3 to 9 hydroxyl (OH) groups.

They may be chosen, alone or as mixtures, from:

- triols, such as trimethylolethane or trimethylolpropane;
- tetraols such as pentaerythritol (tetramethylolmethane), erythritol, diglycerol or ditrimethylolpropane;
- pentols such as arabitol;
- hexols such as dulcitol, sorbitol, mannitol, dipentaerythritol or triglycerol;
- heptols such as volemitol;
- octaols;
- nonanols such as isomalt, maltitol, isomaltitol or lactitol.

Preferably, the polyol is chosen from sorbitol, maltitol, mannitol and isomalt, and mixtures thereof.

Among the water-soluble carbohydrates and water-soluble polyols in accordance with the invention, the ones that will more particularly be chosen are water-soluble oligo- and polysaccharides and more preferentially dextrans, *pullulans*, glucose syrups and maltodextrins and better still glucose syrups with a D.E. ranging from 21 to 38 and/or maltodextrins with a D.E. ranging from 4 to 20 and better still maltodextrins with a D.E. ranging from 12 to 20.

Use will preferably be made of glucose syrups such as those sold by Tereos under the names G210, G290 and G380 and potato or corn maltodextrins such as those sold under the trade names MD 20P® from Avebe and Maldex 120®, Maldex 170® and Maldex 190® from Tereos.

The water-soluble carbohydrate(s) and/or polyol(s) in accordance with the invention represent from 10% to 80% by weight, preferably from 15% to 70% by weight, more preferentially from 20% to 65% by weight and better still from 40% to 60% by weight relative to the total weight of the envelope of the particle.

According to a particularly preferred form of the invention, the envelope of the particles according to the invention is formed from

- at least one starch ($C_5$-$C_{20}$)alkenyl succinate and
- at least one maltodextrin with a D.E. ranging from 4 to 20 and preferably ranging from 12 to 20 and/or a glucose syrup with a D.E. ranging from 21 to 60 and preferentially from 21 to 38.

According to a first variant, the envelope of the particles according to the invention is formed from at least one starch ($C_5$-$C_{20}$)alkenyl succinate and from at least one maltodextrin with a D.E. ranging from 4 to 20 and preferably ranging from 12 to 20.

According to a second variant, the envelope of the particles according to the invention is formed from at least one starch ($C_5$-$C_{20}$)alkenyl succinate and from at least one glucose syrup with a D.E. ranging from 21 to 60 and preferentially ranging from 21 to 38.

According to a particularly preferred form of the invention, the envelope of the particles with release of beneficial agent is formed from a) at least one starch ($C_5$-$C_{20}$)alkenyl succinate in an amount ranging from 20% to 90% by weight, especially from 30% to 80% by weight, preferably from 40% to 70% by weight and better still from 40% to 60% by weight relative to the total weight of the envelope of the particle and b) at least one glucose syrup with a D.E. ranging from 21 to 38 and/or a maltodextrin with a D.E. ranging from 4 to 20 in an amount ranging from 10% to 80% by weight, preferably from 15% to 70% by weight, more preferentially from 20% to 65% by weight and better still from 40% to 60% by weight relative to the total weight of the envelope of the particle.

According to a particularly preferred form of the invention, the envelope of the particles with release of beneficial agent is formed from a) at least one starch ($C_5$-$C_{20}$)alkenyl succinate in an amount ranging from 20% to 90% by weight, especially from 30% to 80% by weight, preferably from 40% to 70% by weight and better still from 40% to 60% by weight relative to the total weight of the envelope of the particle and b) at least one maltodextrin with a D.E. ranging from 4 to 20 in an amount ranging from 10% to 80% by weight, preferably from 15% to 70% by weight, more preferentially from 20% to 65% by weight and better still from 40% to 60% by weight relative to the total weight of the envelope of the particle.

According to a particularly preferred form of the invention, the envelope of the particles with release of beneficial agent is formed from a) at least one starch ($C_5$-$C_{20}$)alkenyl succinate in an amount ranging from 20% to 90% by weight, especially from 30% to 80% by weight, preferably from 40% to 70% by weight and better still from 40% to 60% by weight relative to the total weight of the envelope of the particle and b) at least one glucose syrup with a D.E. ranging from 21 to 38 in an amount ranging from 10% to 80% by weight, preferably from 15% to 70% by weight, more preferentially from 20% to 65% by weight and better still from 40% to 60% by weight relative to the total weight of the envelope of the particle.

Process for Preparing the Encapsulation Particles

The particles according to the invention may especially be prepared according to the process described in patent EP 1 917 098 B1 from FeyeCon.

According to a particular form of the invention, the particles are obtained according to a process comprising at least the following steps:

- an aqueous solution formed from a mixture of the water-soluble carbohydrate and/or the water-soluble polyol and of the hydrophobically modified polysaccharide is prepared, the beneficial agent is then added and the whole is stirred so as to form an emulsion; and
- said emulsion thus formed is homogenized at high pressure at a pressure ranging from 10 to 200 bar and more preferentially from 20 to 200 bar;
- said emulsion is sprayed, preferably continuously, in a drying chamber; and
- the water is extracted for a time preferably not exceeding 3 hours, and more preferentially not exceeding 30 minutes, with a fluid under pressure such as carbon dioxide, preferably in supercritical form, preferably at a pressure of at least 0.3 XPc and at a temperature of at least Tc-60° C. with Pc corresponding to the critical pressure of the gas and Tc the critical temperature of the gas, so as to obtain particles, which are preferably spherical, with a mean size preferably ranging from 1 to 150 μm, more preferentially ranging from 2 to 100 μm and better still from 5 to 80 μm.

Structuring Agent

The compositions according to the invention comprise at least one structuring agent, which may preferably be chosen from waxes, pasty compounds, and mineral or organic lipophilic gelling agents, and mixtures thereof.

It is understood that the amount of these compounds may be adjusted by a person skilled in the art so as not to harm the desired effect in the context of the present invention.

Pasty Fatty Substance

For the purposes of the present invention, the term "pasty fatty substance" (also known as pasty fatty substance) means a lipophilic fatty compound with a reversible solid/liquid change of state, having anisotropic crystal organization in the solid state, and comprising a liquid fraction and a solid fraction at a temperature of 23° C.

In other words, the starting melting point of the pasty compound may be less than 23° C. The liquid fraction of the pasty compound measured at 23° C. may represent 9% to 97% by weight of the compound. This fraction that is liquid at 23° C. preferably represents between 15% and 85% and more preferably between 40% and 85% by weight.

Within the meaning of the invention, the melting point corresponds to the temperature of the most endothermic peak observed on thermal analysis (DSC) as described in Standard ISO 11357-3: 1999. The melting point of a pasty substance or of a wax may be measured using a differential scanning calorimeter (DSC), for example the calorimeter sold under the name MDSC 2920 by the company TA Instruments.

The measuring protocol is as follows:

A sample of 5 mg of pasty substance or wax (depending on the case) placed in a crucible is subjected to a first temperature rise passing from −20° C. to 100° C., at the heating rate of 10° C./minute, then is cooled from 100° C. to −20° C. at a cooling rate of 10° C./minute and finally subjected to a second temperature rise passing from −20° C. to 100° C. at a heating rate of 5° C./minute. During the second temperature rise, the variation in the difference between the power absorbed by the empty crucible and the crucible containing the sample of pasty substance or wax as a function of the temperature is measured. The melting point of the compound is the temperature value corresponding to the top of the peak of the curve representing the variation in the difference in power absorbed as a function of the temperature.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound in order to pass from the solid state to the liquid state. The pasty compound is said to be in the solid state when all of its mass is in the crystalline solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5° C. or 10° C. per minute, according to the standard ISO 11357-3; 1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., formed from a liquid fraction and a solid fraction.

The liquid fraction of the pasty compound measured at 32° C. preferably represents from 30% to 100% by weight of the compound, preferably from 50% to 100% and more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same way as the heat of fusion consumed at 23° C.

The pasty compound is preferably chosen from synthetic compounds and compounds of plant origin. A pasty compound may be obtained via synthesis from starting materials of plant origin.

The pasty compound is advantageously chosen from:

- lanolin and derivatives thereof,
- polyol ethers chosen from pentaerythrityl ethers of a polyalkylene glycol, fatty alkyl ethers of a sugar, and mixtures thereof, the pentaerythrityl ether of polyethylene glycol comprising 5 oxyethylene units (5 OE) (CTFA name: PEG-5 Pentaerythrityl Ether), polypropylene glycol pentaerythrityl ether comprising 5 oxypropylene (5 OP) units (CTFA name: PEG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio corresponding to 46% of PEG-5 pentaerythrityl ether, 46% of PPG-5 pentaerythrityl ether and 8% of soybean oil, polymeric or non-polymeric silicone compounds, polymeric or non-polymeric fluoro compounds, vinyl polymers, especially:

olefin homopolymers and copolymers, hydrogenated diene homopolymers and copolymers, linear or branched homopolymer or copolymer oligomers of alkyl (meth)acrylates preferably containing a $C_8$-$C_{30}$ alkyl group, homopolymer and copolymer oligomers of vinyl esters containing $C_8$-$C_{30}$ alkyl groups, homopolymeric and copolymeric oligomers of vinyl ethers containing $C_8$-$C_{30}$ alkyl groups, liposoluble polyethers resulting from the polyetherification between one or more $C_2$-$C_{100}$ and preferably $C_2$-$C_{50}$ diols, esters, and/or mixtures thereof.

The pasty compound is preferably a polymer, especially a hydrocarbon-based polymer.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of propylene oxide to the alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Among the esters, the following are especially preferred:

esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol, the arachidyl propionate sold under the brand name Waxenol 801 by Alzo, phytosterol esters, fatty acid triglycerides and derivatives thereof, pentaerythritol esters, non-crosslinked polyesters resulting from polycondensation between a linear or branched $C_4$-$C_{50}$ dicarboxylic acid or polycarboxylic acid and a $C_2$-$C_{50}$ diol or polyol, ester aliphatic esters resulting from the esterification of an aliphatic hydroxycarboxylic acid ester with an aliphatic carboxylic acid. Preferably, the aliphatic carboxylic acid comprises from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups.

The aliphatic hydroxycarboxylic acid ester is chosen from:

a) partial or total esters of saturated linear monohydroxylated aliphatic monocarboxylic acids;

b) partial or total esters of unsaturated monohydroxylated aliphatic monocarboxylic acids;

c) partial or total esters of saturated monohydroxylated aliphatic polycarboxylic acids;

d) partial or total esters of saturated polyhydroxylated aliphatic polycarboxylic acids;

e) partial or total esters of $C_2$ to $C_{16}$ aliphatic polyols that have reacted with a monohydroxylated or polyhydroxylated aliphatic monocarboxylic or polycarboxylic acid, and mixtures thereof.

esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl/isostearyl/cetyl/stearyl/behenyl dimer dilinoleate (Plandool H or Plandool S), and mixtures thereof, hydrogenated rosinate esters, such as dilinoleyl dimers of hydrogenated rosinate (Lusplan DD-DHR or DD-DHR from Nippon Fine Chemical);

and mixtures thereof.

Wax(es)

According to a preferred embodiment, the composition according to the invention comprises at least one wax.

The wax under consideration in the context of the present invention is generally a lipophilic compound that is solid at room temperature (25° C.), with a solid/liquid reversible change of state, having a melting point of greater than or equal to 30° C., which may be up to 200° C. and in particular up to 120° C.

In particular, the waxes that are suitable for use in the invention may have a melting point of greater than or equal to 45° C. and in particular greater than or equal to 55° C.

The waxes that may be used in the compositions according to the invention are chosen from waxes that are solid at room temperature, of animal, plant, mineral or synthetic origin, and mixtures thereof.

Examples that may be mentioned include the following hydrocarbon-based waxes comprising a fatty alkyl chain generally containing from 10 to 60 carbon atoms and preferably from 20 to 40 carbon atoms, said chain possibly being saturated or unsaturated, substituted or unsubstituted, and linear, branched or cyclic, preferably saturated and linear:

fatty alcohols that are solid at room temperature (25° C.), such as stearyl alcohol or cetyl alcohol or mixtures thereof, fatty alcohol esters, fatty acids, fatty acid am ides, fatty acid esters including triglycerides, fatty acid ethers, ethoxylated fatty alcohols, ethoxylated fatty acids and the corresponding salts thereof.

Among the fatty alcohols, mention may be made of stearyl alcohol and cetearyl alcohol, or mixtures thereof.

Among the fatty alcohol esters, mention may be made of triisostearyl citrate, ethylene glycol bis(12-hydroxystearate), tristearyl citrate, stearyl octanoate, hexyldecyl stearate, stearyl heptanoate and trilauryl citrate, and mixtures thereof.

Among the fatty acid esters, mention may be made of ester waxes, monoglycerides, diglycerides and triglycerides.

Ester waxes that may be mentioned include stearyl stearate, stearyl behenate, stearyloctyldodecanol, cetearyl behenate, behenyl behenate, ethylene glycol distearate and ethylene glycol dipalmitate. Use may be made in particular of a C20-C40 alkyl (hydroxystearyloxy)stearate (the alkyl group containing from 20 to 40 carbon atoms), alone or as a mixture. Such a wax is especially sold under the names Kester Wax K 82 P®, Hydroxypolyester K 82 P® and Kester Wax K 80 P® by the company Koster Keunen.

Among the triglyceride waxes, mention may be made more particularly of tribehenin, $C_{18}$-$C_{36}$ triglycerides, and mixtures thereof.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Mention may especially be made, among these waxes, of isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S® by the company Heterene.

Mention may also be made of silicone waxes ($C_{30-45}$ alkyl dimethicone) and fluorinated waxes.

The waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

As microwaxes that may be used in the compositions according to the invention, mention may be made especially of carnauba microwaxes, such as the product sold under the name MicroCare 350® by the company Micro Powders, synthetic microwaxes, such as the product sold under the name MicroEase 1145® by the company Micro Powders, microwaxes consisting of a mixture of carnauba wax and polyethylene wax, such as the products sold under the names Micro Care 300® and 310® by the company Micro Powders, microwaxes consisting of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

Lipophilic Gelling Agents

Mineral Gelling Agents

Mineral lipophilic gelling agents that may be mentioned include optionally modified clays, for instance hectorites modified with a $C_{10}$ to $C_{22}$ ammonium chloride, for instance hectorite modified with distearyldimethylammonium chloride, for instance the product sold under the name Bentone 38V® by the company Elementis.

Mention may also be made of fumed silica optionally hydrophobically treated at the surface, the size of the particles of which is less than 1 μm. This is because it is possible to chemically modify the surface of the silica, by chemical reaction generating a reduction in the number of silanol groups present at the surface of the silica. It is especially possible to substitute silanol groups with hydrophobic groups: a hydrophobic silica is then obtained. The hydrophobic groups may be trimethylsiloxyl groups, which are obtained especially by treating fumed silica in the presence of hexamethyldisilazane. Silicas thus treated are known as "silica silylate" according to the CTFA (8th Edition, 2000). They are sold, for example, under the references Aerosil R812® by the company Degussa, CAB-O-SIL TS-530® by the company Cabot, dimethylsilyloxyl or polydimethylsiloxane groups, which are obtained especially by treating fumed silica in the presence of polydimethylsiloxane or dimethyldichlorosilane. Silicas thus treated are known as "silica dimethyl silylate" according to the CTFA (8th Edition, 2000). They are sold, for example, under the references Aerosil R972® and Aerosil R974® by the company Degussa and Cab-O-Sil TS-610® and Cab-O-Sil TS-720® by the company Cabot.

The hydrophobic fumed silica in particular has a particle size that may be nanometric to micrometric, for example ranging from about 5 to 200 nm.

Organic Gelling Agents

The polymeric organic lipophilic gelling agents are, for example, partially or totally crosslinked elastomeric organopolysiloxanes of three-dimensional structure, for instance those sold under the names KSG6®, KSG16® and KSG18® from Shin-Etsu, Trefil E-505C® or Trefil E-506C® from Dow Corning, Gransil SR-CYC®, SR DMF10®, SR-DC556®, SR SCYC Gel®, SR DMF 10 Gel® and SR DC 556 Gel® from Grant Industries and SF 1204® and JK 113® from General Electric; ethylcellulose, for instance the product sold under the name Ethocel® by Dow Chemical; galactomannans comprising from one to six and in particular from two to four hydroxyl groups per saccharide, substituted with a saturated or unsaturated alkyl chain, for instance guar gum alkylated with C1 to C6, and in particular C1 to C3, alkyl chains, and mixtures thereof. Block copolymers of "diblock", "triblock" or "radial" type, of the polystyrene/polyisoprene or polystyrene/polybutadiene type, such as the products sold under the name Luvitol HSB® by the company BASF, of the polystyrene/copoly(ethylene-propylene) type, such as the products sold under the name Kraton® by the company Shell Chemical Co., or of the polystyrene/copoly(ethylene-butylene) type, and mixtures of triblock and radial (star) copolymers in isododecane, such as those sold by the company Penreco under the name Versagel®, for instance the mixture of butylene/ethylene/styrene triblock copolymer and of ethylene/propylene/styrene star copolymer in isododecane (Versagel M 5960).

Lipophilic gelling agents that may also be mentioned include polymers with a weight-average molecular mass of less than 100 000, comprising a) a polymer backbone with hydrocarbon-based repeating units containing at least one heteroatom, and optionally b) at least one optionally functionalized pendent fatty chain and/or terminal fatty chain, containing from 6 to 120 carbon atoms and being linked to these hydrocarbon-based units, as described in patent applications WO-A-02/056 847 and WO-A-02/47619, the content of which is incorporated by reference; in particular, polyamide resins (especially comprising alkyl groups containing from 12 to 22 carbon atoms) such as those described in U.S. Pat. No. 5,783,657, the content of which is incorporated by reference. Mention may be made in particular of a mixture of copolymers of a C36 diacid condensed onto ethylenediamine; the terminal ester groups result from the esterification of the remaining acid end groups with cetyl alcohol, stearyl alcohol or mixtures thereof (also known as cetylstearyl alcohol) (INCI name: Ethylenediamine/stearyl dimer dilinoleate copolymer). Its weight-average molecular mass is preferably 6000. These mixtures are especially sold by the company Arizona Chemical under the trade names Uniclear 80 and Uniclear 100 VG. They are sold, respectively, in the form of a gel at 80% (of active material) in a mineral oil, and at 100% (of active material). They have a softening point of 88° C. to 94° C.

According to the lipophilic gelling agents that may be used in the compositions according to the invention, mention may also be made of polymers derived from a monomer containing a crystallizable chain chosen from saturated $C_{14}$ to $C_{22}$ alkyl (meth)acrylates and even more particularly poly(stearyl acrylate)s or poly(behenyl acrylate)s. By way of example, mention may be made of the polymers having the INCI name "Poly C10-30 alkyl acrylate", for instance the Intelimer® products from the company Air Products, for instance the product Intelimer® IPA 13-1, which is a polystearyl acrylate, or the product Intelimer® IPA 13-6, which is a behenyl polymer.

Among the lipophilic gelling agents that may be used in the compositions according to the invention, mention may also be made of fatty acid esters of dextrin, such as dextrin palmitates, especially the products sold under the name Rheopearl TL® or Rheopearl KL® by the company Chiba Flour.

It is also possible to use silicone polyamides of the polyorganosiloxane type, such as those described in documents U.S. Pat. Nos. 5,874,069, 5,919,441, 6,051,216 and U.S. Pat. No. 5,981,680.

These silicone polymers may belong to the following two families:

- polyorganosiloxanes comprising at least two groups capable of establishing hydrogen interactions, these two groups being in the chain of the polymer, and/or
- polyorganosiloxanes comprising at least two groups capable of establishing hydrogen interactions, these two groups being located on grafts or branches.

Among the structuring agents, use will be made more preferentially of pasty substances, waxes and organic gelling agents such as beeswax, lanolin wax, carnauba wax, candelilla wax, orange and lemon waxes, microcrystalline waxes, paraffins, ozokerite, polyethylene waxes, fatty acid triglycerides, stearyl alcohol, cetearyl alcohol, cetylstearyl alcohol, isomerized jojoba oil, hydrogenated sunflower oil, hydrogenated castor oil, hydrogenated coconut oil, hexyldecyl stearate, and a mixture of soybean sterols and of oxyethylenated (5 OE) oxypropylenated (5 OP) pentaerythritol, and mixtures thereof.

Even more preferentially, the structuring agents will be chosen from cetylstearyl alcohol, carnauba waxes, candelilla wax, polyethylene waxes, hydrogenated castor oil, the mixture of soybean sterols and of oxyethylenated (5 OE) oxypropylenated (5 OP) pentaerythritol, sold under the reference Lanolide by the company, Vevy, ozokerite and hexyldecyl stearate, and mixtures thereof.

The structuring agent(s) are present in amounts preferably ranging from 1% to 70% and more particularly from 4% to 60% relative to the total weight of the composition, and even more preferentially from 8% to 50%.

Fatty Phase

According to a particular form of the invention, the composition comprises at least one fatty phase, especially in a proportion of from 15% to 95% by weight and more particularly from 30% to 85% by weight relative to the total weight of the composition.

The fatty phase preferably comprises at least one compound chosen from volatile or nonvolatile carbon-based, hydrocarbon-based, fluoro and/or silicone oils, waxes and/or solvents of animal, plant or synthetic origin, alone or as a mixture, provided that they form a stable, homogeneous mixture and are compatible with the intended use.

For the purposes of the invention, the term "volatile" refers to any compound that is capable of evaporating on contact with keratin materials, in less than one hour, at room temperature (25° C.) and atmospheric pressure (1 atm). This volatile compound especially has a nonzero vapor pressure, at room temperature and atmospheric pressure, especially ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

In contrast, the term "non-volatile" refers to a compound which remains on human keratin materials at room temperature and atmospheric pressure, for at least one hour, and which especially has a vapor pressure of less than $10^{-3}$ mmHg (0.13 Pa).

Presentation Forms

The compositions according to the invention are in any solid form, especially in the form of wands (sticks), cakes, pellets, etc. In this regard, they contain the ingredients generally used in products of this type, which are well known to those skilled in the art.

Beneficial Agents

The amount of beneficial agent present in the particles in accordance with the invention preferably ranges from 0.1% to 80% by weight relative to the weight of the particle, preferably from 1% to 70% by weight, better still from 10% to 60% and even better still from 15% to 50% by weight relative to the total weight of the particle.

The time for release of the beneficial agent will obviously vary according to the nature and intensity of the stimulus.

The total duration for release of the beneficial agent may be modified and will depend greatly on the composition, the content of particles, the nature and especially the chemical nature of the beneficial agent and its concentration in the particles (amount encapsulated in the particle) and the nature and intensity of the stimulus to which the particle containing the beneficial agent will be subjected. The release may equally be virtually instantaneous or last several hours or even several days.

Among the beneficial agents that may be used according to the invention, mention may be made more particularly of:

(i) fatty substances;

(ii) fragrancing substances;

(iii) pharmaceutical active principles;
(iv) cosmetic active agents.

a) Fatty Substances

They may be chosen from the group comprising
(i) natural oils of plant, animal or marine origin,
(ii) mineral oils,
(iii) hydrogenated oils,
(iv) silicone oils,
(v) terpenes,
(vi) squalene,
(vii) saturated or unsaturated fatty acids,
(viii) fatty acid esters,
(x) waxes,
(x) fatty alcohols,
(xi) butters such as shea butter or cocoa butter,
(xii) and mixtures thereof.

b) Fragrancing Substances

The term "fragrancing substance" means any ingredient that is capable of giving off a pleasant odor.

Perfumes are compositions especially containing starting materials (generally referred to as perfumery ingredients) described in S. Arctander, Perfume and Flavor Chemicals (Montclair, N.J., 1969), in S. Arctander, Perfume and Flavor Materials of Natural Origin (Elizabeth, N.J., 1960) and in Flavor and Fragrance Materials—1991, Allured Publishing Co., Wheaton, Ill.

They may be synthetic products or natural products, for instance essential oils, absolutes, resinoids, resins, concretes, and/or synthetic products (terpene or sesquiterpene hydrocarbons, alcohols, phenols, aldehydes, ketones, ethers, acids, esters, nitriles or peroxides, which may be saturated or unsaturated, and aliphatic or cyclic).

According to the definition given in international standard ISO 9235 and adopted by the Commission of the European Pharmacopoeia, an essential oil is an odoriferous product generally of complex composition, obtained from a botanically defined plant raw material, either by steam entrainment, or by dry distillation, or via an appropriate mechanical process without heating. The essential oil is generally separated from the aqueous phase via a physical process which does not result in any significant change in the composition.

Among the essential oils that may be used according to the invention, mention may be made of those obtained from plants belonging to the following botanical families:

Abietaceae or Pinaceae: conifers; Amaryllidaceae; Anacardiaceae; Anonaceae: ylang ylang; Apiaceae (for example Umbelliferae): dill, angelica, coriander, sea fennel, carrot, parsley; Araceae; Aristolochiaceae; Asteraceae: yarrow, artemisia, camomile, helichrysum; Betulaceae; Brassicaceae; Burseraceae: frankincense; Caryophyllaceae; Canellaceae; Cesalpiniaceae: copaifera (copaiba balsam); Chenopodaceae; Cistaceae: rock rose; Cyperaceae; Dipterocarpaceae; Ericaceae: gaultheria (wintergreen); Euphorbiaceae; Fabaceae; Geraniaceae: geranium; Guttiferae; Hamamelidaceae; Hernandiaceae; Hypericaceae: St-John's wort; Iridaceae; Juglandaceae; Lamiaceae: thyme, oregano, monarda, savory, basil, marjorams, mints, patchouli, lavenders, sages, catnip, rosemary, hyssop, balm; Lauraceae: ravensara, sweet bay, rosewood, cinnamon, *litsea*; Liliaceae: garlic; lily, lily of the valley, hyacinth, daffodil; Magnoliaceae: magnolia; Malvaceae; Meliaceae; Monimiaceae; Moraceae: hemp, hop; Myricaceae; Myristicaceae: nutmeg; Myrtaceae: eucalyptus, tea tree, paperbark tree, cajuput, backhousia, clove, myrtle; Oleaceae; Piperaceae: pepper; Pittosporaceae; Poaceae: lemon balm, lemongrass, vetiver; Polygonaceae; Renonculaceae; Rosaceae: roses; Rubiaceae; Rutaceae: all citrus plants; Salicaceae; Santalaceae: sandalwood; Saxifragaceae; Schisandraceae; Styracaceae: benzoin; Thymelaceae: agarwood; Tilliaceae; Valerianaceae: valerian, spikenard; Verbenaceae: lantana, verbena; Violaceae; Zingiberaceae: galangal, turmeric, cardamom, ginger; Zygophyllaceae.

Mention may also be made of the essential oils extracted from flowers (lily, lavender, rose, jasmine, ylang ylang, neroli), from stems and leaves (patchouli, geranium, petitgrain), from fruit (raspberry, peach, coriander, aniseed, cumin, juniper), from fruit peel (bergamot, lemon, orange, grapefruit), from roots (angelica, celery, cardamom, iris, sweet flag, ginger), from wood (pinewood, sandalwood, gaiac wood, rose of cedar, camphor), from grasses and gramineae (tarragon, rosemary, basil, lemongrass, sage, thyme), from needles and branches (spruce, fir, pine, dwarf pine) and from resins and balms (galbanum, elemi, benzoin, myrrh, olibanum, opopanax).

Examples of fragrancing substances are especially: geraniol, geranyl acetate, farnesol, borneol, bornyl acetate, linalool, linalyl acetate, linalyl propionate, linalyl butyrate, tetrahydrolinalool, citronellol, citronellyl acetate, citronellyl formate, citronellyl propionate, dihydromyrcenol, dihydromyrcenyl acetate, tetrahydromyrcenol, terpineol, terpinyl acetate, nopol, nopyl acetate, nerol, neryl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, cis-3-hexenyl acetate, vetiveryl acetate, ethyl acetate, butyl acetate, hexyl acetate, decyl acetate, isoamyl acetate, stearyl acetate, allyl heptanoate, vetiverol, α-hexylcinnamaldehyde, 2-methyl-3-(p-tert-butylphenyl)propanal, 2-methyl-3-(p-isopropylphenyl)propanal, 3-(p-tert-butylphenyl)propanal, 2,4-dimethylcyclohex-3-enylcarboxaldehyde, tricyclodecenyl acetate, tricyclodecenyl propionate, allyl 3-cyclohexylpropionate, ethyl 6-(acetyloxy)hexanoate, allyl caproate, ethyl 2 methylbutyrate, methyl dihydrojasmonate, hexyl salicylate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetrahydropyran, 3-carboxymethyl-2-pentylcyclopentane, 2-n-4-heptylcyclopentanone, 3-methyl-2-pentyl-2-cyclopentenone, menthone, carvone, tagetone, geranyl acetone, n-decanal, n-dodecanal, anisylpropanal, 9-decen-1-ol, cis-3-hexenol, tetrahydro-2-isobutyl-4-methylpyran-4-ol, 3-methyl-5-phenyl-1-pentanol, 3a,6,6,9a-tetramethyldodecahydronaphtho[2,1-b]furan, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepinonitrile, aubepine, heliotropin, coumarin, eugenol, vanillin, diphenyl ether, citral, citronellal, hydroxycitronellal, hexylcinnamal, 2,4-dimethylcyclohex-3-ene-1-carbaldehyde, 2,6-dimethylhept-5-enal, α,α-dimethyl-p-ethylphenylpropanal, 1,3-benzodioxole-5-carboxaldehyde, limonene, damascone, decalactone, nonalactone, 6,6-dimethoxy-2,5,5-trimethylhex-2-ene, 2,4,4,7-tetramethyloct-6-en-3-one, 1-(5,5-dimethyl-1-cyclohexenyl)pent-4-en-1-one, methylheptenone, 4-(cyclopropylmethyl)phenyl methyl ether, 2-methyl-6-methylideneoct-7-en-2-ol, rose oxide, 1-(1,2,3,4,5,6,7,8-octahydro-2,3,8,8-tetramethyl-2-naphthyl)ethan-1-one, 2-acetonaphthone, 2-isopropyl-5-methylcyclohexanone, ionones, methylionones, isomethylionones, solanone, irones, cis-3-hexenol and esters thereof, indane musks, tetralin musks, isochroman musks, macrocyclic ketones, macrolactone musks, aliphatic musks, ethylene brassylate, rose essence, and mixtures thereof.

In general, perfumes are formed from a mixture of perfumery ingredients which may also be classified into head notes, heart notes and base notes.

The three notes correspond to the greater or lesser volatility of the ingredients of which they are composed: highly volatile head note, moderately volatile heart note and sparingly volatile base note.

(i) The head note, also known as the "top" note, is that which is first perceived by the sense of smell as soon as the perfume comes into contact with the keratin material or any substrate. However, it is the note which fades the fastest: it does not "last". It is difficult to express the time of persistence of this note, since it is very variable: from a few minutes to about 10 minutes.

It is essentially fresh and light. All the citrus notes especially fall into this category. In perfumery, they are grouped under the generic term hesperidean notes, which include orange, lemon, grapefruit, bergamot, neroli, etc. Mention will also be made of herbal notes such as lavender, laurel, thyme or rosemary, and aniseed, menthol, aldehyde, etc. notes. Mention will also be made of eucalyptus notes.

(ii) The heart note, also occasionally referred to as the "body note", has a persistence which lasts from a few tens of minutes to a few hours, but its main characteristic is that it is not perceived until after a few minutes. Thus, it "starts" just before the head note dies off. It begins to express itself while the head note gradually fades away. It is represented essentially by floral, fruity or spicy elements: lily of the valley, honeysuckle, violet, magnolia, cinnamon, geranium, jasmine, rose, iris, raspberry, peach, etc.

(iii) The base note, also occasionally known as the "bottom note", gives a perfume its "durability", persistence or staying power. It is perceptible several hours, or even several days, or even several weeks after application onto clothing or a perfume blotter or scent strip, depending on the concentration of the perfume. Examples that will be mentioned include woods, roots, mosses and resins and animal or mineral substances such as opoponax, musks, amber, sandalwood, benzoin, lichen, clove, sage, etc. Mention will also be made of vanilla, patchouli, coumarin, etc. notes.

Needless to say, ingredients belonging to one or more notes may be encapsulated. However, it will be preferred to encapsulate the most volatile ingredients (i.e. the least persistent) belonging to the head and/or heart notes. Among these ingredients, examples that will be mentioned include:

benzyl acetate
geranyl acetate
cis-3-hexenyl acetate
C18 aldehyde or nonalactone
decyl acetate
allyl amyl glycolate (citral)
ethyl acetate
butyl acetate
allyl 3-cyclohexylpropionate
linalyl acetate
phenylethyl alcohol
hexyl acetate
Berryflor or ethyl 6-(acetyloxy)hexanoate
isoamyl acetate
allyl caproate
Amarocite or 6,6-dimethoxy-2,5,5-trimethylhex-2-ene
Citral lemarome N or 3,7-dimethylocta-2,6-dienal
Canthoxal or anisylpropanal
Claritone or 2,4,4,7-tetramethyloct-6-en-3-one
ethyl 2-methylbutyrate
dihydromyrcenol
cis-3-hexenol
hedione or methyl dihydrojasmonate
L-carvone
allyl heptanoate
limonene
neobutenone alpha or 1-(5,5-dimethyl-1-cyclohexenyl)pent-4-en-1-one
methylheptenone
Toscanol or 4-(cyclopropylmethyl)phenyl methyl ether
Myrcenol Super or 2-methyl-6-methylideneoct-7-en-2-ol
decalactone
stearyl acetate
rose oxide
linalool
Triplal or 2,4-dimethylcyclohex-3-ene-1-carbaldehyde
Melonal or 2,6-dimethylhept-5-enal
1-(1,2,3,4,5,6,7,8-octahydro-2,3,8,8-tetramethyl-2-naphthyl)ethan-1-one hexylcinnamal
tetrahydro-2-isobutyl-4-methylpyran-4-ol
hexyl salicylate
1,4-dioxacycloheptadecane-5,17-dione
and mixtures thereof.

According to a particular form of the invention, the encapsulation particles comprise at least one or more fragrancing substances with a saturating vapor pressure at 25° C. of greater than or equal to 10.0 Pa.

The saturating vapor pressure (or vapor tension) is the pressure at which the gaseous phase of a substance is in equilibrium with its liquid or solid phase at a given temperature in a closed system. Calculation of the saturating vapor pressure may be performed using the following formula:

$$\ln\frac{p_{sat}}{p_0} = \frac{M, L_v}{R}\left(\frac{1}{T_0} - \frac{1}{T}\right)$$

with:

$T_0$: boiling point of the substance at a given pressure $p_0$, in degrees Kelvin, $p_{sat}$: saturating vapor pressure, in the same unit as $p_0$ M: molar mass of the substance, in kg/mol $L_v$: latent heat of vaporization of the substance, in joules/kg R: ideal gas constant, equal to 8.31447 J/K/mol T: temperature of the vapor, in K.

Preferably, the fragrancing substances with a saturating vapor pressure at 25° C. of greater than or equal to 10 Pa represent an amount ranging from 50% to 100% by weight, preferably from 60% to 100% by weight, more preferentially from 70% to 100% by weight and better still from 80% to 100% by weight relative to the total weight of the fragrancing substances present in the particles of the invention.

c) Pharmaceutical Active Principles

The term "pharmaceutical active principle" means a molecule or a mixture of molecules which has a curative and/or prophylactic therapeutic effect, which can be administered by spraying.

d) Cosmetic Active Agents

The term "cosmetic active agent" means any molecule which has a hygiene, care, makeup or coloring effect contributing toward the improvement, well-being and/or enhancement or modification of the appearance of the human keratin material onto which said composition is applied.

Among the cosmetic active agents that may be applied to human keratin materials such as the skin, the lips, the scalp, the hair, the eyelashes or the nails, examples that may be mentioned, alone or as mixtures, include:

- vitamins and derivatives or precursors thereof, alone or as mixtures;
- antioxidants;
- cleaning agents such as surfactants;
- dyestuffs;
- conditioning agents;
- agents for relaxing and/or straightening and/or shaping the hair;
- free-radical scavengers;
- photoprotective agents such as organic or mineral UV-screening agents;
- self-tanning agents;
- anti-glycation agents;
- calmatives;
- hair-removing agents;
- deodorant agents;
- antiperspirants;
- NO-synthase inhibitors;
- agents for stimulating fibroblast proliferation;
- agents for stimulating keratinocyte proliferation;
- dermo-relaxing agents,
- refreshing agents;
- tensioning agents,
- matting agents;
- skin-shine counteractants;
- anti-seborrhea agents;
- greasy-hair counteractants;
- depigmenting agents;
- pro-pigmenting agents;
- keratolytic agents;
- desquamating agents;
- moisturizers;
- antimicrobial agents;
- slimming agents;
- agents that act on the energy metabolism of cells;
- insect repellents;
- substance P or CGRP antagonists;
- hair-loss counteractants;
- antiwrinkle agents;
- antiaging agents;
- antidandruff agents.

Among these cosmetic active agents, preference will be given most particularly, alone or as mixtures, to:

- photoprotective agents such as UV-screening agents, in particular organic UV-screening agents;
- skin-shine counteractants;
- anti-seborrhea agents;
- greasy-hair counteractants;
- deodorant agents;
- antiperspirants;
- refreshing agents;
- matting agents;
- antimicrobial agents;
- antidandruff agents.

According to a particularly preferred form of the invention, the beneficial agent(s) present in the particles will be chosen from fragrancing substances.

According to a particular form of the invention, the composition will comprise:

a) particles containing at least one fragrancing substance and b) at least one fragrancing substance in free form, which may be identical to or different from the fragrancing substance present in said particles.

Said fragrancing substances in free form may be chosen from those mentioned previously.

According to another particular form of the invention, the composition exclusively contains the fragrancing substance(s) in the encapsulation particles. In other words, all of the ingredients for fragrancing that are present in the composition are contained in the particles.

A person skilled in the art may select the appropriate composition, and also the method for preparing it, on the basis of his general knowledge, taking into account firstly the nature of the constituents used, and secondly the intended application of the composition.

According to a particular form of the invention, the compositions according to the invention are makeup products in which the composition comprises at least one coloring agent in free form and/or in encapsulated form, chosen especially from nacres, pigments and reflective particles, and mixtures thereof. These products may especially be lipsticks, foundations cast in stick or dish form, face powders, eyeshadows, concealer sticks, lip glosses, eyeliners or mascaras. More particularly, the release particles comprise at least one fragrancing substance. Even more particularly, the compositions will also contain a fragrancing substance in free form, which may be identical to or different from the fragrancing substance present in the particles.

Coloring Agents

According to a particular form of the invention, the pulverulent phase advantageously comprises at least one coloring agent. This pulverulent phase preferably comprises more generally at least one coloring agent chosen from nacres, pigments and reflective particles, and mixtures thereof.

Said composition advantageously has a content of coloring agent, and in particular of pigment(s), of greater than or equal to 0.01% by weight relative to the total weight of the composition.

Pigments

The term "pigments" should be understood as meaning white or colored, mineral or organic particles of any form, which are insoluble in the physiological medium and are intended to color the composition.

The pigments may be white or colored, and mineral and/or organic.

Among the mineral pigments, mention may be made of titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminum powder and copper powder.

The organic pigments may be chosen from the materials below, and mixtures thereof:

cochineal carmine, organic pigments of azo dyes, anthraquinone dyes, indigoid dyes, xanthene dyes, pyrene dyes, quinoline dyes, triphenylmethane dyes and fluoran dyes.

Among the organic pigments, mention may be made in particular of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The chemical materials corresponding to each of the organic dyestuffs mentioned previously are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

A composition according to the invention may comprise a content of pigments ranging from 0 to 30% by weight relative to the total weight of the composition, preferably ranging from 2% to 20% by weight and preferentially ranging from 4% to 10% by weight, relative to the total weight of the composition.

Nacres

The terms "nacres" should be understood as meaning colored particles of any form, which may or may not be iridescent, especially produced by certain molluscs in their shell, or alternatively synthesized, and which have a color effect via optical interference.

Examples of nacres that may be mentioned include nacreous pigments such as titanium mica coated with an iron oxide, mica coated with bismuth oxychloride, titanium mica coated with chromium oxide, and nacreous pigments based on bismuth oxychloride. They may also be mica particles, at the surface of which are superposed at least two successive layers of metal oxides and/or of organic dyestuffs.

The nacres may more particularly have a yellow, pink, red, bronze, orange, brown, gold and/or coppery color or glint.

As illustrations of nacres that may be introduced into the composition, mention may be made of the gold-colored nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper glint sold especially by the company Engelhard under the name Copper 340A (Timica); the nacres with a red glint sold especially by the company Merck under the name Sienna fine (17386) (Colorona); the nacres with a yellow glint sold especially by the company Engelhard under the name Yellow (4502) (Chromalite); the red nacres with a gold glint sold especially by the company Engelhard under the name Sunstone G012 (Gemtone); the pink nacres sold especially by the company Engelhard under the name Tan opale G005 (Gemtone); the black nacres with a gold glint sold especially by the company Engelhard under the name Nu antique bronze 240 AB (Timica), the blue nacres sold especially by the company Merck under the name Matte blue (17433) (Microna), the white nacres with a silvery glint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles comprising a glass substrate coated with titanium oxide are sold in particular under the name Metashine MC1080RY by the company Toyal.

Finally, examples of nacres that may also be mentioned include polyethylene terephthalate flakes, especially those sold by the company Meadowbrook Inventions under the name Silver 1P 0.004X0.004 (silver flakes).

The compositions according to the invention may have a nacre content ranging from 0 to 30% by weight, for example from 0.01% to 5% by weight relative to the total weight of the composition.

Reflective Particles

The term "reflective particles" denotes particles whose size, structure, especially the thickness of the layer(s) of which they are made and their physical and chemical nature, and surface state, allow them to reflect incident light. This reflection may, if appropriate, have an intensity sufficient to create, at the surface of the composition or mixture, when the latter is applied to the substrate to be made up, highlight points visible to the naked eye, that is to say more luminous points which contrast with their surroundings by appearing to sparkle.

The reflective particles may be selected so as not to significantly alter the coloration effect generated by the coloring agents with which they are combined, and more particularly so as to optimize this effect in terms of color rendition. They may more particularly have a yellow, pink, red, bronze, orange, brown, gold and/or coppery color or glint.

These particles may have varied forms and may especially be in platelet or globular form, in particular in spherical form.

Irrespective of their form, the reflective particles may or may not have a multilayer structure, and, in the case of a multilayer structure, may have, for example, at least one layer of uniform thickness, especially of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or mineral materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material. Reflective particles are described especially in documents JP-A-09188830, JP-A-10158450, JP-A-10158541, JP-A-07258460 and JP-A-05017710.

Mention may also be made, still by way of example of reflective particles comprising a mineral substrate coated with a layer of metal, of the particles comprising a borosilicate substrate coated with silver.

Particles comprising a glass substrate coated with silver, in the form of platelets, are sold under the name Microglass Metashine REFSX 2025 PS by Toyal. Particles with a glass substrate coated with nickel/chromium/molybdenum alloy are sold under the name Crystal Star GF 550 and GF 2525 by this same company.

Use may also be made of particles comprising a metal substrate, such as silver, aluminum, iron, chromium, nickel, molybdenum, gold, copper, zinc, tin, magnesium, steel, bronze or titanium, said substrate being coated with at least one layer of at least one metal oxide, such as titanium oxide, aluminum oxide, iron oxide, cerium oxide, chromium oxide, silicon oxides and mixtures thereof.

Examples that may be mentioned include aluminum powder, bronze powder or copper powder coated with $SiO_2$ sold under the name Visionaire by the company Eckart.

The compositions according to the invention may have a content of reflective particles ranging from 0 to 30% by weight, for example from 0.01% to 5% by weight, relative to the total weight of the composition.

Preferably, the coloring agents are chosen from:

- organic pigments advantageously chosen from the pigments certified D&C by the Food & Drug Administration as listed in the section "Color Additives—Batch Certified by the U.S. Food and Drug Administration" of the CTFA; mention may be made especially of Blue 1 and 4, Brown 1, Ext. Violet 2, Ext. Yellow 7, Green 3, 5, 6 and 8, Orange 4, 5, 10 and 11, Red 4, 6, 7, 17, 21, 22, 27, 28, 30, 36 and 40, Violet 2, Yellow 5, 6, 7, 8, 10 and 11, and mixtures thereof,
- mineral pigments advantageously chosen from iron oxide, titanium oxide, zirconium oxide, cerium oxide, zinc oxide or chromium oxide, ferric blue, manganese violet, ultramarine blue, pink or violet, chromium hydrate, chromium hydroxide and bismuth oxychloride, and mixtures thereof.

According to a particular form of the invention, the compositions according to the invention are skincare products especially for the face or the lips, in which the composition comprises at least one cosmetic or dermatological active agent. These products may especially be lipcare balms or bases, daily care balms or bases, or alternatively antisun or self-tanning sticks. More particularly, the release particles comprise at least one fragrancing substance. Even more particularly, the compositions will also contain a fragrancing substance in free form, which may be identical to or different from the fragrancing substance present in the particles.

According to another particular form of the invention, the compositions according to the invention may be in the form of deodorants and/or antiperspirants in free form and/or in encapsulated form, in which the composition comprises at least one deodorant active agent and/or at least one antiperspirant active agent. More particularly, the release particles comprise at least one fragrancing substance. Even more particularly, the compositions will also contain a fragrancing substance in free form, which may be identical to or different from the fragrancing substance present in the particles.

This embodiment has the advantage of releasing, almost immediately after rupture of the particles on contact with water or sweat, a fragrancing substance intended to provide a fresh effect.

Antiperspirant Active Agent

The term "antiperspirant active agent" refers to a compound which, by itself, has the effect of reducing the flow of sweat and/or of reducing the sensation on the skin of moisture associated with human sweat and/or of partially or totally absorbing human sweat.

Among the antiperspirant active agents, mention may be made of aluminum and/or zirconium salts such as aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, alum salts, aluminum sulfate, aluminum zirconium octachlorohydrate, aluminum zirconium pentachlorohydrate, aluminum zirconium tetrachlorohydrate, aluminum zirconium trichlorohydrate and more particularly the aluminum chlorohydrate in activated or nonactivated form sold by the company Reheis under the name Microdry Aluminum Chlorohydrate® or by the company Guilini Chemie under the name Aloxicoll PF 40. Aluminum and zirconium salts are, for example, the product sold by the company Reheis under the name Reach AZP-908-SUF®, "activated" aluminum salts, for example the product sold by the company Reheis under the name Reach 103 or by the company Westwood under the name Westchlor 200.

Preferably, the cosmetic composition comprises aluminum chlorohydrate as antiperspirant active agent.

As other antiperspirant active agent, mention may be made of expanded perlite particles such as those obtained by the expansion process described in U.S. Pat. No. 5,002,698.

The perlites that may be used according to the invention are generally aluminosilicates of volcanic origin and have the composition:

70.0-75.0% by weight of silica $SiO_2$ 12.0-15.0% by weight of oxide of aluminum oxide $Al_2O_3$ 3.0-5.0% of sodium oxide $Na_2O$ 3.0-5.0% of potassium oxide $K_2O$ 0.5-2% of iron oxide $Fe_2O_3$ 0.2-0.7% of magnesium oxide MgO 0.5-1.5% of calcium oxide CaO 0.05-0.15% of titanium oxide $TiO_2$ Preferably, the perlite particles used will be ground; in this case, they are known as Expanded Milled Perlite (EMP). They preferably have a particle size defined by a median diameter D50 ranging from 0.5 to 50 μm and preferably from 0.5 to 40 μm.

Preferably, the perlite particles used have a loose bulk density at 25° C. ranging from 10 to 400 $kg/m^3$ (standard DIN 53468) and preferably from 10 to 300 $kg/m^3$.

Preferably, the expanded perlite particles according to the invention have a water absorption capacity, measured at the wet point, ranging from 200% to 1500% and preferably from 250% to 800%.

The wet point corresponds to the amount of water that needs to be added to 100 g of particles in order to obtain a homogeneous paste. This method is directly derived from the oil uptake method applied to solvents. The measurements are taken in the same manner by means of the wet point and the flow point, which have, respectively, the following definitions:

Wet point: mass expressed in grams per 100 g of product corresponding to the production of a homogeneous paste during the addition of a solvent to a powder.

Flow point: mass expressed in grams per 100 g of product above which the amount of solvent is greater than the capacity of the powder to retain it. This is reflected by the production of a more or less homogeneous mixture which flows over the glass plate.

The wet point and the flow point are measured according to the following protocol:

Protocol for Measuring the Water Absorption

1) Equipment Used

Glass plate (25×25 mm)

Spatula (wooden shaft and metal part, 15×2.7 mm)

Silk-bristled brush

Balance

2) Procedure

The glass plate is placed on the balance and 1 g of perlite particles is weighed out. The beaker containing the solvent and the liquid sampling pipette is placed on the balance. The solvent is gradually added to the powder, the whole being regularly blended (every 3 to 4 drops) by means of the spatula.

The mass of solvent needed to obtain the wet point is noted. Further solvent is added and the mass which makes it possible to reach the flow point is noted. The average of three tests will be determined.

The expanded perlite particles sold under the trade names Optimat 1430 OR or Optimat 2550 by the company World Minerals will be used in particular.

Deodorant Active Agents

The term "deodorant active agent" refers to any substance that is capable of masking, absorbing, improving and/or reducing the unpleasant odor resulting from the decomposition of human sweat by bacteria.

The deodorant active agents may be bacteriostatic agents or bactericides that act on underarm odor microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, polyols such as those of glycerol type, 1,3-propanediol (Zemea Propanediol sold by DuPont Tate & Lyle Bio Products), 1,2-decanediol (Symclariol from the company Symrise), glycerol derivatives, for instance caprylic/capric glycerides (Capmul MCM from Abitec), glyceryl caprylate or caprate (Dermosoft GMCY and Dermosoft GMC, respectively from Straetmans), Polyglyceryl-2 caprate (Dermosoft DGMC from Straetmans), biguanide derivatives, for instance polyhexamethylene biguanide salts; chlorhexidine and salts thereof; 4-phenyl-4,4-dimethyl-2-butanol (Symdeo MPP from Symrise); cyclodextrins; chelating agents such as Tetrasodium Glutamate Diacetate (CAS #51981-21-6) sold under the trade name Dissolvine GL-47-S from AkzoNobel, EDTA (ethylenediaminetetraacetic acid) and DPTA (1,3-diaminopropanetetraacetic acid).

Among the deodorant active agents in accordance with the invention, mention may also be made of:

- zinc salts, such as zinc salicylate, zinc phenolsulfonate, zinc pyrrolidonecarboxylate (more commonly known as zinc pidolate), zinc sulfate, zinc chloride, zinc lactate, zinc gluconate, zinc ricinoleate, zinc glycinate, zinc carbonate, zinc citrate, zinc chloride, zinc laurate, zinc oleate, zinc orthophosphate, zinc stearate, zinc tartrate, zinc acetate or mixtures thereof;
- odor absorbers such as zeolites, especially silver-free metal zeolites, cyclodextrins, metal oxide silicates such as those described in patent application US 2005/063 928; metal oxide particles modified with a transition metal, as described in patent applications US 2005/084 464 and US 2005/084 474, aluminosilicates such as those described in patent application EP 1 658 863, chitosan-based particles such as those described in U.S. Pat. No. 6,916,465;
- sodium bicarbonate;
- salicylic acid and derivatives thereof such as 5-n-octanoylsalicylic acid;
- alum;
- triethyl citrate.

The deodorant active agents may be present in the compositions according to the invention in weight proportions of about 0.01% to 10% by weight relative to the total weight of the composition.

The present invention also relates to a cosmetic process for treating body odor and optionally human perspiration, which consists in applying to the surface of a keratin material a composition as defined previously comprising at least one deodorant active agent and/or antiperspirant active agent.

The invention is illustrated in greater detail in the examples that follow.

EXAMPLES OF PREPARING PARTICLES WITH RELEASE OF PERFUME

Example A

Capsules were prepared using the following composition:

| | Composition | | | |
|---|---|---|---|---|
| | Hydrophobically modified starch | Water-soluble polysaccharide | Fragrance* | Water |
| Example A | Amidon Capsul ® from National Starch 110 g | Potato maltodextrin MD 20 P from Avebe 110 g | 55 g | 225 g |

* The perfume used has the following composition:

| Ingredients | Amount in g |
|---|---|
| Isopropyl myristate | 20.5 |
| Methyl dihydrojasmonate | 15 |
| 2-Phenylethanol | 8 |
| 1-(1,2,3,4,5,6,7,8-Octahydro-2,3,8,8-tetramethyl-2-naphthyl)ethan-1-one | 8 |
| Hexylcinnamal | 6 |
| Tetrahydro-2-isobutyl-4-methylpyran-4-ol | 6 |
| Hexyl salicylate | 6 |
| Benzyl acetate | 5 |
| 1,4-Dioxacycloheptadecane-5,17-dione | 5 |
| 3-Methyl-5-phenyl-1-pentanol | 5 |
| Dihydromyrcenol | 4 |
| Orange terpenes 0.05% BHT (limonene >95%) | 4 |
| 2-Acetonaphthone | 2 |
| 3a,6,6,9a-Tetramethyldodecahydronaphtho[2,1-b]furan | 1 |
| α,α-Dimethyl-p-ethylphenylpropanal | 1 |
| 1,3-Benzodioxole-5-carboxaldehyde | 1 |
| 2-Isopropyl-5-methylcyclohexanone | 1 |
| 1-Phenylethyl acetate | 0.8 |
| 2,6-Dimethylhept-5-enal (Melonal) | 0.5 |
| 2,4-Dimethylcyclohex-3-ene-1-carbaldehyde (Triplal) | 0.2 |

Process for Preparing the Emulsion

Potato maltodextrin MD20P and the starch Capsul® were mixed in water until dissolved, the perfume was then added and the whole was emulsified with a Heidolph Diax 900 Ultra-Turrax disperser (motor power 900 W with an electronically controlled speed of 8000 to 26 000 rpm) at the maximum power for 4 minutes.

Drying Procedure for Obtaining Spherical Particles

The emulsion obtained was then homogenized at a pressure of 30 bar using a high-pressure pump and then sprayed in an atomization chamber using a nozzle simultaneously with a stream of $CO_2$ (30 bar, 45° C.) which was circulated continuously at a flow rate of about 500 g/min to remove the water. The dried powder was retained on a filter located at the base of the atomization chamber, and then collected after depressurization. 270 g of spherical microcapsules in the form of a fine white powder with a number-mean diameter of 7.8 μm and a volume-mean diameter of 47 μm were thus obtained.

The size of the particles was measured via the dry route by laser scattering using a Microtrac S3500 particle size analyzer, the particle sizes being expressed by volume and by number.

| | Measured characteristics of the capsules | | | |
|---|---|---|---|---|
| | Amount of encapsulated perfume (%) | Amount of free perfume (%) | Poured powder density | Absolute density |
| Example A | 19.8 | <0.1 | 484 | 1.12 |

Examples B to H

According to the process described in Example A, the following capsules were prepared:

| | Composition | | | |
|---|---|---|---|---|
| | Hydrophobi-cally modified starch | Water-soluble polysaccharide | Perfume of Example A | Water |
| Example B | Amidon Capsul ® from National Starch 110 g | Maltodextrin MD 120 from Tereos 110 g | 55 g | 225 g |
| Example C | Amidon Capsul ® from National Starch 110 g | Maltodextrin MD 170 from Tereos 110 g | 55 g | 225 g |
| Example D | Amidon Capsul ® from National Starch 110 g | Maltodextrin MD 190 from Tereos 110 g | 55 g | 225 g |
| Example E | Amidon Capsul ® from National Starch 110 g | Potato maltodextrin MD 20 P from Avebe 110 g | 105 g | 225 g |
| Example F | Amidon Capsul ® from National Starch 154 g | Potato maltodextrin MD 20 P from Avebe 66 g | 55 g | 225 g |
| Example G | Amidon Capsul ® from National Starch 66 g | Potato maltodextrin MD 20 P from Avebe 154 g | 55 g | 225 g |
| Example H | Amidon Capsul ® from National Starch 110 g | Glucose syrup Glucodry G290 from Tereos 110 g | 55 g | 225 g |

| | Measured characteristics of the capsules | | | |
|---|---|---|---|---|
| Examples | Amount of encapsulated perfume (%) | Amount of free perfume (%) | Poured powder density (g/l) | Absolute density |
| Example B | 19.3 | <0.1 | 568 | 1.14 |
| Example C | 19.4 | <0.1 | 490 | 1.16 |
| Example D | 19.9 | <0.1 | 537 | 1.11 |
| Example E | 38 | 0.8 | 482 | 1.08 |
| Example F | 21.0 | 0.2 | 595 | 1.11 |
| Example G | 20.7 | 0.2 | 521 | 1.15 |
| Example H | 19.2 | 0.1 | 568 | 1.12 |

Comparative Example I

Capsules having the same composition as Example A as described above were prepared according to the process of Example 1 of U.S. Pat. No. 6,200,949 comprising drying by spray-drying (atomization) of the emulsion.

The emulsion is dried by spray-drying using a Bowen Lab Model Dryer machine using air with a flow rate of 420 $m^3$/h at a temperature of 204° C. and an external temperature of 93° C. and a turbine speed of 50 000 rpm.

Morphological aspect of the particles obtained: polymorph with aggregates.

Comparative Example J

Capsules having the same composition as Example A as described above were prepared according to the process of Example 1 of U.S. Pat. No. 5,508,259 comprising drying by spray-drying (atomization) of the emulsion.

The mixture was dried by spray-drying with a CCM Sulzer machine at an emulsion flow rate of 50 kg/h, air at a flow rate of 320 $m^3$/h at 350° C. and 0.45 bar.

Morphological aspect of the particles obtained: polymorph with aggregates.

| | Measured characteristics of the capsules | | | |
|---|---|---|---|---|
| Composition | Amount of encapsulated perfume (%) | Amount of free perfume (%) | Poured powder density (g/l) | Absolute density |
| Example I (outside the invention) | 18.3 | 2.7 | 259 | 1.16 |
| Example J (outside the invention) | 11.2 | 1.7 | 269 | 1.12 |

FORMULATION EXAMPLES

Example 1

Deodorant and Antiperspirant Product

A deodorant and antiperspirant having the following composition was prepared:

| Ingredients (INCI name) | Amounts in % by weight |
|---|---|
| Oxypropylenated (14 OP) butyl alcohol | 5.9 |
| Isopropyl palmitate | 25.4 |
| Polyethylene glycol distearate (8 OE) | 6.2 |
| Glycine-buffered aluminum/zirconium tetrahydroxychloride complex | 19.0 |
| Calcium hydroxide | 0.5 |
| Polyethylene wax (MW: 500) | 11.4 |
| Polydimethylsiloxane (viscosity: 10 cSt) | 22.2 |
| Ozokerite | 2.6 |
| Perlite (25 microns) | 0.2 |
| Capsules of perfume of Example A | 6.7 |
| TOTAL | 100 |

Isopropyl palmitate and oxypropylenated butyl alcohol are placed in a tank. The mixture is heated to 65° C. and the other ingredients are then added (one by one) while remaining at 65-70° C. The whole is homogenized until a homogeneous solution is obtained, for about 15 minutes. The perlite and the perfume capsules of Example A are added and the mixture is then cooled to about 55° C. (a few ° C. above the thickening point of the mixture) and poured into sticks, which are stored in a refrigerator at 4° C. for 30 minutes.

Examples C1 and C2

In a manner similar to that of Example 1, deodorant antiperspirant sticks having the following compositions were prepared:

| Example C1 (outside the invention) | |
|---|---|
| Ingredients | (% by weight) |
| Oxypropylenated butyl alcohol | 5.9 |
| Isopropyl palmitate | 25.4 |
| Polyethylene glycol distearate | 6.2 |
| Glycine-buffered aluminum/zirconium tetrahydroxychloride complex | 19.0 |
| Calcium hydroxide | 0.5 |
| Polyethylene wax | 11.4 |
| PDMS | 22.2 |
| Ozokerite | 2.6 |
| Perlite | 0.2 |
| Capsules of perfume of Example I | 6.7 |
| TOTAL | 100 |

| Example C2 (outside the invention) | |
|---|---|
| Ingredients | (% by weight) |
| Oxypropylenated butyl alcohol | 5.9 |
| Isopropyl palmitate | 25.4 |
| Polyethylene glycol distearate | 6.2 |
| Glycine-buffered aluminum/zirconium tetrahydroxychloride complex | 19.0 |
| Calcium hydroxide | 0.5 |
| Polyethylene wax | 11.4 |
| PDMS | 22.2 |
| Ozokerite | 2.6 |
| Perlite | 0.2 |
| Capsules of perfume of Example J | 6.7 |
| TOTAL | 100 |

Evaluation of the Examples
Evaluation Protocol:

About 0.2 g of composition was deposited uniformly onto a perfume blotter (reference from Granger Veyron: 40140BCSI of size 4 cm×14 cm). After 1 minute, the perfume odor intensity was evaluated. Perspiration was then simulated by adding about 0.1 g of water (three sprays) onto the deposited composition. After waiting for 1 minute, the blotter was smelled again.

| Formulation | Odor intensity BEF | Odor intensity AFT |
|---|---|---|
| Example 1 | Odorless | Very strong perfume odor |
| Example C1 | Strong perfume odor | Very strong perfume odor |
| Example C2 | Strong perfume odor | Strong perfume odor |

BEF = before addition of water;
AFT = after addition of water

It was thus observed at $T_0$ that the formula of Example 1 comprising the perfume capsules according to the invention has no odor before the addition of water, in contrast with Examples C1 and C2 (outside the invention), which shows that the perfume capsules in Examples C1 and C2 are not leaktight before the addition of water.

It was also observed that the composition of Example, 1 after stimulation with water, led to a very intense odor, which demonstrates substantial release of perfume in response to the water stimulus.

Example 2

Preparation of an Antiperspirant Stick Having the Following Composition

| Ingredients | Amounts in weight % |
|---|---|
| Cyclopentasiloxane (DC245 - Dow Corning) | 20.0 |
| Hexyldecyl stearate (Eutanol G16 S - Cognis) | 14.0 |
| PPG-14 butyl ether | 5.0 |
| Hydrogenated castor oil (Cutina HR - Cognis) | 6.0 |
| Cetearyl alcohol | 8.0 |
| Cetearyl alcohol/Ceteareth-30 80/20 (Sinnowax AO - Cognis) | 14.0 |
| Talc | 7.0 |
| Microdry Aluminum Chlorohydrate ® | 20.0 |
| Capsules of perfume of Example G | 6.0 |
| Total | 100 |

The capsules of perfume of Example G may be replaced with the capsules of Examples A to F and H described previously.

The cyclopentasiloxane is heated to 65° C. The other ingredients are added (one by one), while remaining at 65-70° C. The whole is homogenized (transparent solution) for 15 minutes. The two deodorant active agents and the capsules of Example G are added. The mixture is cooled to about 55° C. (a few ° C. above the thickening point of the mixture) and poured into sticks, which are stored in a refrigerator at 4° C. for 30 minutes.

The intensity of the perfume odor on the skin was evaluated at T0, T2h and T6h after application of the composition.

About 0.15 g of the composition of Example 2 was applied to the skin. After 1 minute, the intensity of the perfume odor was evaluated (BEF), and was graded from 0 to 10. About 0.1 g of water (three sprays) were then sprayed onto the composition applied to the skin. After waiting for 30 seconds, the intensity of the perfume odor was evaluated (AFT).

2 and 6 hours later, the intensity of the odor was re-evaluated (BEF) before adding about 0.1 g of water (three sprays) to the composition applied to the skin. After waiting for 30 seconds, the intensity of the odor was evaluated (AFT).

| | Odor intensity T0h | | | Odor intensity T2h | | | Odor intensity T6h | | |
|---|---|---|---|---|---|---|---|---|---|
| Product | BEF | AFT | Δ | BEF | AFT | Δ | BEF | AFT | Δ |
| Example 2 | 1.0 | 5.0 | 4 | 3.0 | 5.5 | 2.5 | 2.5 | 4.5 | 2.0 |

BEF = before addition of water;
AFT = after addition of water
Δ = amplitude of difference in olfactory intensity (BEF − AFT)
Scale of perfume odor intensity: 0 to 10 (0 = odorless; 10 = very intense/saturated odor).

It was thus observed at T0 that, on the skin, the composition of Example 2 has a virtually odorless odor. It was also observed that each spraying of water onto the product at T0, T2h and T6h leads to an increase in the perfume odor intensity, which demonstrates substantial release of perfume.

Example 3

In a manner similar to that of Example 2, an antiperspirant stick having the following composition was prepared:

| Ingredients | % by weight |
|---|---|
| Cyclopentasiloxane (DC245 - Dow Corning) | 20.6 |
| Hexyldecyl stearate (Eutanol G16 S - Cognis) | 14.0 |
| PPG-14 butyl ether | 5.0 |
| Hydrogenated castor oil (Cutina HR - Cognis) | 6.0 |
| Cetearyl alcohol | 8.0 |
| Cetearyl alcohol/Ceteareth-30 80/20 (Sinnowax AO - Cognis) | 14.0 |
| Talc | 7.0 |
| Aluminium chlorohydrate (Micro Dry) | 20.0 |
| Capsules of perfume of Example A | 5.0 |
| Free perfume | 0.4 |
| Total | 100 |

The capsules of perfume of Example A may be replaced with the capsules of Examples B to H described previously.

The intensity of the perfume odor on the skin was evaluated at T0, T2h and T6h after application of the composition according to the protocol described in Example 2.

| | Odor intensity T0h | | | Odor intensity T2h | | | Odor intensity T6h | | |
|---|---|---|---|---|---|---|---|---|---|
| Product | BEF | AFT | Δ | BEF | AFT | Δ | BEF | AFT | Δ |
| Example 3 | 5.0 | 6.5 | 1.5 | 4.0 | 6.0 | 2.0 | 3.0 | 6.0 | 3.0 |

It was thus observed at T0 that the composition of Example 3 has a perfume odor of moderate intensity. It was also observed at each time (T0, T2h and T6h) that the spraying of water onto the product leads to an increase in the perfume odor intensity (especially of the fresh notes), which demonstrates substantial release of perfume.

Example 4

Preparation of an Antiperspirant Stick Having the Following Composition

| Ingredients | % by weight |
|---|---|
| Polyethylene wax (Performalene 500-L polyethylene (New Phase Technologies) | 4.1 |
| Ethylene homopolymer (Performalene 400 Polyethylene - New Phase Technologies) | 8.3 |
| Cyclohexadimethylsiloxane (Dow Corning 246 Fluid - Dow Corning) | 25.4 |
| Phenyl trimethicone (Dow Corning 556 Cosmetic Grade Fluid - Dow Corning) | 18.6 |
| Isohexadecane | 19.6 |
| Methyl methacrylate crosspolymer (Ganzpearl GMP 0820 - Ganz Chemical) | 13.0 |
| Expanded milled perlite (Optimat 1430 OR - Word Minerals) | 4.5 |
| Micronized zinc pyrrolidonecarboxylate (UCIB - Solabia) | 0.5 |
| Capsules of perfume of Example G | 6.0 |
| Total | 100 |

The capsules of perfume of Example G may be replaced with the capsules of Examples A to F and H described previously.

The cyclohexadimethylsiloxane is heated to 65° C. The other ingredients are added (one by one) while remaining at 65-70° C. The whole is homogenized until a transparent solution is obtained, for about 15 minutes. The zinc pyrrolidonecarboxylate, the perlite and the perfume capsules of Example G are added and the mixture is then cooled to about 55° C. (a few ° C. above the thickening point of the mixture) and poured into sticks, which are stored at 4° C. for 30 minutes.

The composition applied to the armpits leaves a deposit on the skin which gives off a perfume odor. The perfume is released in the course of the day when the capsules are in contact with perspiration.

The invention claimed is:

1. A solid anhydrous composition comprising:

1) particles comprising a core containing at least one beneficial agent and an envelope surrounding the core; said envelope comprising at least one hydrophobically modified polysaccharide chosen from starch ($C_5$-$C_{20}$) alkenyl succinates and at least one water-soluble carbohydrate chosen from maltodextrins;

said particles simultaneously having a poured powder density ranging from 300.0 g/l to 600.0 g/l and an absolute density of greater than 1.0, and wherein the particles are spherical and have a number-mean diameter ranging from 5 to 150 μm; and 2) at least one structuring agent.

2. The composition as claimed in claim 1, comprising a physiologically acceptable medium.

3. The composition as claimed in claim 1, in which the particles have a number-mean diameter ranging from 5 to 10 μm, and a volume-mean diameter ranging from 10 to 100 μm.

4. The composition as claimed in claim 1, in which the hydrophobically modified polysaccharide is sodium starch octenyl succinate.

5. The composition as claimed in claim 1, in which the hydrophobically modified polysaccharide represents from 20% to 90% by weight, relative to the total weight of the envelope of the particle.

6. The composition as claimed in claim 1, in which the water-soluble carbohydrate is chosen from maltodextrins with a D.E. ranging from 12 to 20.

7. The composition as claimed in claim 1, in which the water-soluble carbohydrate(s) represent from 10% to 80% by weight relative to the total weight of the envelope of the particle.

8. The composition as claimed in claim 1, in which the envelope of the particles with release of beneficial agent is formed from at least one starch ($C_5$-$C_{20}$)alkenyl succinate and from at least one maltodextrin with a D.E. ranging from 4 to 20.

9. The composition as claimed in claim 8, in which the envelope of the particles with release of beneficial agent is formed from a) 20% to 90% by weight relative to the total weight of the envelope of the particle, and b) at least one maltodextrin with a D.E. ranging from 4 to 20 in an amount ranging from 10% to 80% by weight relative to the total weight of the envelope of the particle.

10. The composition as claimed in claim 1, in which the structuring agent is chosen from beeswax, lanolin wax, carnauba wax, candelilla wax, orange and lemon waxes, microcrystalline waxes, paraffins, ozokerite, polyethylene waxes, fatty acid triglycerides, stearyl alcohol, cetearyl alcohol, cetylstearyl alcohol, isomerized jojoba oil, hydrogenated sunflower oil, hydrogenated castor oil, hydrogenated coconut oil, hexyldecyl stearate, a mixture of soybean sterols and of oxyethylenated (5 OE) oxypropylenated (5 OP) pentaerythritol, and mixtures thereof.

11. The composition as claimed claim 1, in which the particles with release of beneficial agent is obtained according to a process comprising at least the following steps:

an aqueous solution formed from a mixture of the water-soluble carbohydrate and/or the water-soluble polyol and of the hydrophobically modified polysaccharide is prepared, the beneficial agent is then added and the whole is stirred so as to form an emulsion; and said emulsion thus formed is homogenized at high pressure at a pressure ranging from 10 to 200 bar;

said emulsion is sprayed in a drying chamber; and the water is extracted for a time preferably not exceeding 3 hours, and more preferentially not exceeding 30 minutes, with a fluid under pressure so as to obtain particles with release of beneficial agent.

12. The composition as claimed in claim 1, in which the beneficial agents are chosen from:

(i) fatty substances;

(ii) fragrancing substances;

(iii) pharmaceutical active principles;

(iv) cosmetic active agents.

13. The composition as claimed in claim 1, in which the beneficial agents are chosen from fragrancing substances.

14. The composition as claimed in claim 1, in which the particles comprise at least one or more fragrancing substances with a saturating vapor pressure at 25° C. of greater than or equal to 10.0 Pa and said fragrancing substance(s) represent from 50% to 100% by weight relative to the total weight of the fragrancing substances present in the particles.

15. The composition as claimed in claim 1, wherein a) the particles comprise at least one fragrancing substance and b) the composition also comprises at least one fragrancing substance in free form, which may be identical to or different from said fragrancing substance present in said particles.

16. The composition as claimed in claim 1, wherein it exclusively contains one or more fragrancing substances encapsulated in the particles.

17. The composition as claimed in claim 1, comprising at least one coloring agent chosen from nacres, pigments, reflective particles, and mixtures thereof.

18. The composition as claimed in claim 1, comprising at least one deodorant active agent and/or at least one antiperspirant active agent in free form and/or in encapsulated.

19. A process for caring for and/or for the hygiene of and/or for conditioning and/or for fragrancing and/or for making up a human keratin material, which comprises applying to said human keratin material a composition as claimed in claim 1.

20. A cosmetic process for treating body odor and optionally human perspiration, which comprises applying to a keratin material a composition as claimed in claim 17.

21. A consumer product, wherein it is formed from a composition as claimed claim 1.

* * * * *